United States Patent [19]

Doria et al.

[11] 4,444,773
[45] Apr. 24, 1984

[54] SUBSTITUTED THIAZOLO[3,2-A]PYRIMIDINES AND PROCESS FOR THEIR PREPARATION

[75] Inventors: Gianfederico Doria, Milan; Carlo Passarotti, Gallarate; Giuliana Arcari; Ada Buttinoni, both of Milan, all of Italy

[73] Assignee: Farmitalia Carlo Erba S.p.A., Milan, Italy

[21] Appl. No.: 398,302

[22] Filed: Jul. 14, 1982

[30] Foreign Application Priority Data

Jul. 15, 1981 [GB] United Kingdom ............... 8121979
Jan. 20, 1982 [GB] United Kingdom ............... 8201621
Apr. 29, 1982 [GB] United Kingdom ............... 8212430

[51] Int. Cl.³ ............... C07D 513/04; A61K 31/505
[52] U.S. Cl. ............... 424/251; 544/278; 544/281; 544/282; 548/190
[58] Field of Search ............... 544/278, 282; 424/251; 542/431

[56] References Cited

U.S. PATENT DOCUMENTS 3,594,378 7/1971 Laliberte ............... 544/278
3,888,983 6/1975 Baetz ............... 544/278

FOREIGN PATENT DOCUMENTS 43-15981 7/1968 Japan ............... 544/278

*Primary Examiner*—Mary C. Lee
*Assistant Examiner*—S. A. Gibson
*Attorney, Agent, or Firm*—Murray and Whisenhunt

[57] ABSTRACT

Pharmacologically active thiazolo[3,2-a]pyrimidines of the formula

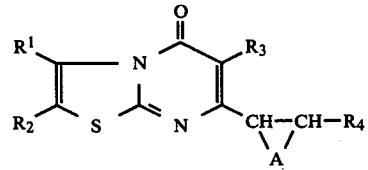

wherein A is a bond between the α and β-carbon atoms or ($-CH_2-$) group; $R_1$ and $R_2$ represent hydrogen or halogen, $C_1-C_4$ alkyl, cyano, $CF_3$, thienyl, pyridyl, biphenyl, naphtyl, phenyl optionally substituted,

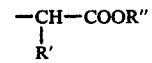

wherein R' and R" are hydrogen or alkyl; $R_3$ represents hydrogen, halogen, alkyl, OH, formyloxy, alkanoyloxy, alkenyloxy; $R_4$ represents pyridyl optionally substituted by alkyl. The compounds have antiinflammatory, anti-ulcerogenic and anti-gastric secretory activity.

14 Claims, No Drawings

SUBSTITUTED THIAZOLO[3,2-A]PYRIMIDINES AND PROCESS FOR THEIR PREPARATION

The present invention relates to substituted thiazolo[3,2-a]pyrimidines, to a process for their preparation and to pharmaceutical compositions containing them. The invention provides compounds having the following general formula (I)

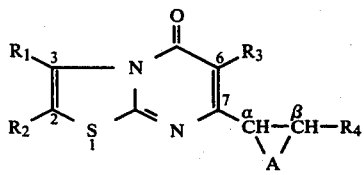
(I)

wherein
A completes a bond, thereby providing a double bond between the α- and β-carbon atoms, or
A represents a —CH$_2$— group, thereby providing a cyclopropane ring including the α- and β-carbon atoms;
each of R$_1$ and R$_2$ independently represents:
(a) a hydrogen or a halogen atom;
(b) C$_1$–C$_4$ alkyl, cyano or trifluoromethyl;
(c) thienyl, pyridyl, biphenyl or naphtyl;
(d) a phenyl group, unsubstituted or substituted by 1 to 3 substituents chosen from halogen, C$_1$–C$_4$ alkyl, hydroxy, C$_1$–C$_4$ alkoxy, formyloxy, C$_2$–C$_8$ alkanoyloxy, trifluoromethyl, nitro, amino, formylamino, C$_2$–C$_8$ alkanoylamino;
(e) a phenyl group substituted by one or two C$_1$–C$_4$ alkylenedioxy groups, wherein the oxygen atoms are linked to two adjacent carbon atoms of the phenyl ring;
(f) a group

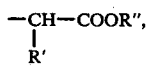

wherein each of R' and R" independently represents a hydrogen atom or a C$_1$–C$_4$ alkyl group;
R$_3$ represents:
(a') a hydrogen or halogen atom;
(b') C$_1$–C$_4$ alkyl;
(c') hydroxy, formyloxy or C$_2$–C$_8$ alkanoyloxy;
(d') C$_1$–C$_4$ alkoxy or C$_3$–C$_4$ alkenyloxy;
R$_4$ represents:
(a") a pyridyl group, which may be unsubstituted or substituted by C$_1$–C$_4$ alkyl;
(b") a group

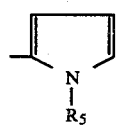

wherein R$_5$ represents a hydrogen atom or a C$_1$–C$_4$ alkyl group;
(c") a group of formula

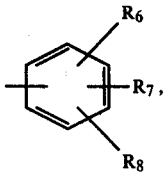

wherein each of R$_6$, R$_7$ and R$_8$ independently represents a hydrogen or a halogen atom; a hydroxy group; a C$_1$–C$_6$ alkoxy group unsubstituted or substituted by C$_1$–C$_4$ dialkylamino group; a C$_1$–C$_4$ alkyl group; formyloxy or a C$_2$–C$_8$ alkanoyloxy group; a —NO$_2$ group or a group

wherein each of R$_9$ and R$_{10}$ independently represents a hydrogen atom, a C$_1$–C$_4$ alkyl group, formyl or a C$_2$–C$_8$ alkanoyl group;
(d") a thiazolyl group, which may be unsubstituted or substituted by C$_1$–C$_4$ alkyl.

The compounds of the invention include also the pharmaceutically acceptable salts of the compounds of formula (I) the metabolites and metabolic precursors of the compounds of formula (I), as well as all possible isomers (e.g. cis or trans isomers and optical isomers) and the mixtures thereof. Preferably the

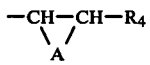

moiety, wherein A and R$_4$ are as defined above, is in the trans configuration. The alkyl, alkoxy, alkenyloxy, alkanoyl and alkanoyloxy groups may be branched or straight chain groups. When R$_1$ and/or R$_2$ are a C$_1$–C$_4$ alkyl group, they are preferably a C$_1$–C$_2$ alkyl group.

When R$_1$ and/or R$_2$ are a phenyl ring substituted as defined above, the phenyl ring is preferably substituted by one or two substituents chosen from chlorine, fluorine, methyl, methoxy, hydroxy, C$_1$–C$_2$ alkylenedioxy and amino.

When one or more of R$_1$, R$_2$ and R$_3$ are a halogen atom, they are preferably chlorine or bromine.

When R$_3$ is C$_1$–C$_4$ alkoxy, it is preferably methoxy or ethoxy. When R$_3$ is C$_1$–C$_4$ alkyl, it is preferably methyl, ethyl or propyl; When one or both of R$_9$ and R$_{10}$ is a C$_2$–C$_8$ alkanoyl group, it is for example acetyl, propionyl, butyryl, valeryl and isovaleryl, preferably it is acetyl and propionyl. When R$_4$ is substituted pyridyl, it is preferably substituted by a methyl group.

When R$_4$ is substituted thiazolyl, it is preferably substituted by a methyl group. When R$_5$ is a C$_1$–C$_4$ alkyl group it is preferably a methyl or ethyl group. When one or more of R$_3$, R$_6$, R$_7$ and R$_8$ represents a C$_2$–C$_8$ alkanoyloxy group, it is for example acetoxy, propionyloxy and butyryloxy; preferably it is acetoxy.

Preferably R' and R" are hydrogen or a C$_1$–C$_2$ alkyl group. When one or more of R$_6$, R$_7$ and R$_8$ is a C$_1$–C$_6$ alkoxy group, it is preferably a methoxy or an ethoxy group. When one or more of R$_6$, R$_7$ and R$_8$ is a C$_1$–C$_4$ alkyl group, it is preferably a methyl group. When one or more of R$_6$, R$_7$ and R$_8$ is a halogen atom, it is preferably chlorine, fluorine or iodine. Preferred compounds of the invention are the compounds of formula (I) wherein A is as defined above; $R_1$ is hydrogen, $C_1$-$C_2$ alkyl, trifluoromethyl, carboxymethyl, pyridyl, biphenyl, naphtyl or phenyl, the phenyl being unsubstituted or substituted as defined above; $R_2$ is hydrogen, chlorine, bromine, $C_1$-$C_2$ alkyl, cyano, or phenyl, unsubstituted or substituted as defined above; $R_3$ is hydrogen, chlorine, bromine, $C_1$-$C_3$ alkyl or $C_1$-$C_2$ alkoxy; and $R_4$ represents (a'''') a pyridyl group unsubstituted or substituted by a methyl group; (b'''') a phenyl group unsubstituted or substituted by one or two substituents selected from $C_1$-$C_2$ alkyl, chlorine, iodine, hydroxy, $C_1$-$C_3$ alkoxy, amino, acetylamino and acetoxy; (c'''') a thiazolyl group, unsubstituted or substituted by $C_1$-$C_2$ alkyl; and the pharmaceutically acceptable salts thereof. Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine, di-(2-ethylhexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic acids, e.g. hydrochloric, hydrobromic sulphuric and nitric acids and with organic acids, e.g. citric, tartaric, maleic, malic, fumaric, methanesulphonic and ethanesulphonic acids.

Examples of particularly preferred compounds of the invention are:

7-trans-[2-(3-pyridyl)-ethenyl]-5H-thiazolo[3,2-a]pyrimidine-5-one;
7-trans-[2-(4-methyl-phenyl)-ethenyl]-5H-thiazolo[3,2-a]pyrimidine-5-one;
6-methoxy-7-trans-[2-(3-pyridyl)-ethenyl]-5H-thiazolo[3,2-a]pyrimidine-5-one;
2-cyano-7-trans-[2-(3-pyridyl)-ethenyl]-5H-thiazolo[3,2-a]pyrimidine-5-one;
2-chloro-7-trans-[2-(3-pyridyl)-ethenyl]-5H-thiazolo[3,2-a]pyrimidine-5-one;
2-chloro-7-trans-[2-(2-methyl-5-thiazolyl)-ethenyl]-5H-thiazolo[3,2-a]pyrimidine-5-one;
2-chloro-6-methoxy-7-trans-[2-(3-pyridyl)-ethenyl]-5H-thiazolo[3,2-a]pyrimidine-5-one;
2-chloro-6-methyl-7-trans-[2-(3-pyridyl)-ethenyl]-5H-thiazolo[3,2-a]pyrimidine-5-one;
6-methyl-7-trans-[2-(3-pyridyl)-ethenyl]-5H-thiazolo[3,2-a]pyrimidine-5-one;
3,6-dimethyl-7-trans-[2-(3-pyridyl)-ethenyl]-5H-thiazolo[3,2-a]pyrimidine-5-one;
2,3,6-trimethyl-7-trans-[2-(3-pyridyl)-ethenyl]-5H-thiazolo[3,2-a]pyrimidine-5-one;
6-methyl-2-phenyl-7-trans-[2-(3-pyridyl)-ethenyl]-5H-thiazolo[3,2-a]pyrimidine-5-one;
6-ethyl-7-trans-[2-(3-pyridyl)-ethenyl]-5H-thiazolo[3,2-a]pyrimidine-5-one;
6-methyl-7-trans-[2-(2-pyridyl)-ethenyl]-5H-thiazolo[3,2-a]pyrimidine-5-one;
6-methyl-7-trans-[2-(6-methyl-2-pyridyl)-ethenyl]-5H-thiazolo[3,2-a]pyrimidine-5-one;
6-methyl-7-trans-[2-(4-methyl-phenyl)-ethenyl]-5H-thiazolo[3,2-a]pyrimidine-5-one;
6-methyl-7-trans-[2-(6-methyl-2-pyridyl)-cyclopropyl]-5H-thiazolo[3,2-a]pyrimidine-5-one;
6-methyl-7-trans-[2-(2-pyridyl)-cyclopropyl]-5H-thiazolo[3,2-a]pyrimidine-5-one;
6-methyl-7-trans-[2-(3-pyridyl)-cyclopropyl]-5H-thiazolo[3,2-a]pyrimidine-5-one;
6-chloro-7-trans-(2-phenyl-ethenyl)-5H-thiazolo[3,2-a]pyrimidine-5-one;
2,6-dichloro-7-trans-[2-(3-pyridyl)-ethenyl]-5H-thiazolo[3,2-a]pyrimidine-5-one;
6-chloro-7-trans-[2-(3-pyridyl)-ethenyl]-5H-thiazolo[3,2-a]pyrimidine-5-one;
6-chloro-3-methyl-7-trans-[2-(3-pyridyl)-ethenyl]-5H-thiazolo[3,2-a]pyrimidine-5-one;
6-chloro-2,3-dimethyl-7-trans-[2-(3-pyridyl)-ethenyl]-5H-thiazolo[3,2-a]pyrimidine-5-one;
6-chloro-3-trifluoromethyl-7-trans-[2-(3-pyridyl)-ethenyl]-5H-thiazolo[3,2-a]pyrimidine-5-one;
6-chloro-3-phenyl-7-trans-[2-(3-pyridyl)-ethenyl]-5H-thiazolo[3,2-a]pyrimidine-5-one;
6-chloro-3-(4-fluoro-phenyl)-7-trans-[2-(3-pyridyl)-ethenyl]-5H-thiazolo[3,2-a]pyrimidine-5-one;
6-chloro-3-(4-chloro-phenyl)-7-trans-[2-(3-pyridyl)-ethenyl]-5H-thiazolo[3,2-a]pyrimidine-5-one;
6-chloro-3-(4-methyl-phenyl)-7-trans-[2-(3-pyridyl)-ethenyl]-5H-thiazolo[3,2-a]pyrimidine-5-one;
6-chloro-3-(2-methoxy-phenyl)-7-trans-[2-(3-pyridyl)-ethenyl]-5H-thiazolo[3,2-a]pyrimidine-5-one;
6-chloro-3-(3-methoxy-phenyl)-7-trans-[2-(3-pyridyl)-ethenyl]-5H-thiazolo[3,2-a]pyrimidine-5-one;
6-chloro-3-(4-methoxy-phenyl)-7-trans-[2-(3-pyridyl)-ethenyl]-5H-thiazolo[3,2-a]pyrimidine-5-one;
6-chloro-3-(2-thienyl)-7-trans-[2-(3-pyridyl)-ethenyl]-5H-thiazolo[3,2-a]pyrimidine-5-one;
6-chloro-3-(2-pyridyl)-7-trans-[2-(3-pyridyl)-ethenyl]-5H-thiazolo[3,2-a]pyrimidine-5-one;
6-chloro-3-(3-pyridyl)-7-trans-[2-(3-pyridyl)-ethenyl]-5H-thiazolo[3,2-a]pyrimidine-5-one;
6-chloro-3-(4-pyridyl)-7-trans-[2-(3-pyridyl)-ethenyl]-5H-thiazolo[3,2-a]pyrimidine-5-one;
6-chloro-7-trans-[2-(3-pyridyl)-ethenyl]-5-oxo-5H-thiazolo[3,2-a]pyrimidine-3-acetic acid;
3-(4-amino-phenyl)-7-trans-[2-(3-pyridyl)-ethenyl]-5H-thiazolo[3,2-a]pyrimidine-5-one;
3-phenyl-7-trans-[2-(3-pyridyl)-ethenyl]-5H-thiazolo[3,2-a]pyrimidine-5-one;
3-(4-fluoro-phenyl)-7-trans-[2-(3-pyridyl)-ethenyl]-5H-thiazolo[3,2-a]pyrimidine-5-one;
3-(4-chloro-phenyl)-7-trans-[2-(3-pyridyl)-ethenyl]-5H-thiazolo[3,2-a]pyrimidine-5-one;
3-(4-methyl-phenyl)-7-trans-[2-(3-pyridyl)-ethenyl]-5H-thiazolo[3,2-a]pyrimidine-5-one;
3-(3-methoxy-phenyl)-7-trans-[2-(3-pyridyl)-ethenyl]-5H-thiazolo[3,2-a]pyrimidine-5-one;
3-(4-methoxy-phenyl)-7-trans-[2-(3-pyridyl)-ethenyl]-5H-thiazolo[3,2-a]pyrimidine-5-one;
3-(3,4-dimethoxy-phenyl)-7-trans-[2-(3-pyridyl)-ethenyl]-5H-thiazolo[3,2-a]pyrimidine-5-one;
3-(3,4-ethylenedioxy-phenyl)-7-trans-[2-(3-pyridyl)-ethenyl]-5H-thiazolo[3,2-a]pyrimidine-5-one;
3-(4-biphenylyl)-7-trans-[2-(3-pyridyl)-ethenyl]-5H-thiazolo[3,2-a]pyrimidine-5-one;
3-(2-naphtyl)-7-trans-[2-(3-pyridyl)-ethenyl]-5H-thiazolo[3,2-a]pyrimidine-5-one;
3-(2-pyridyl)-7-trans-[2-(3-pyridyl)-ethenyl]-5H-thiazolo[3,2-a]pyrimidine-5-one;
3-(3-pyridyl)-7-trans-[2-(3-pyridyl)-ethenyl]-5H-thiazolo[3,2-a]pyrimidine-5-one;

3-(4-pyridyl)-7-trans-[2-(3-pyridyl)-ethenyl]-5H-thiazolo[3,2-a]pyrimidine-5-one;

2-methyl-3-phenyl-7-trans-[2-(3-pyridyl)-ethenyl]-5H-thiazolo[3,2-a]pyrimidine-5-one;

3-(4-N-acetyl-amino-phenyl)-7-trans-[2-(3-pyridyl)-ethenyl]-5H-thiazolo[3,2-a]pyrimidine-5-one;

7-trans-[2-(3-pyridyl)-ethenyl]-3-(2-thienyl)-5H-thiazolo[3,2-a]pyrimidine-5-one, and the pharmaceutically accpetable salts thereof.

The compounds of formula (I) can be obtained by a process comprising:

(a) reacting a compound of formula (II)

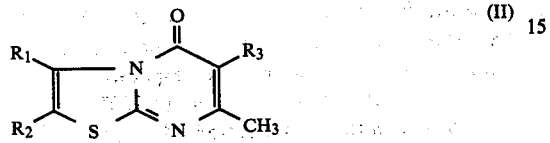

wherein $R_1$, $R_2$ and $R_3$ are as defined above, or a salt thereof, with an aldehyde of formula (III)

R$_4$—CHO        (III)

wherein $R_4$ is as defined above, so obtaining compound of formula (I) wherein A is a bond; or (b) reacting a compound of formula (IV)

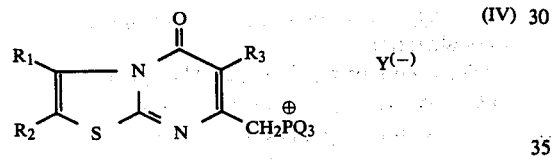

wherein $R_1$, $R_2$ and $R_3$ are as defined above, Q may be aryl or $C_1$-$C_6$ alkyl and $Y^{(-)}$ represents an acidic anion, with an aldehyde of formula (III) as defined above, so obtaining compounds of formula (I) wherein A is bond; or (c) reacting a compound of formula (V)

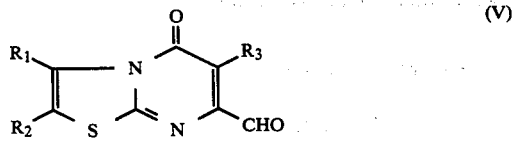

wherein $R_1$, $R_2$ and $R_3$ are as defined above, with a compound of formula (VI)

$R_4$—$CH_2$—$P^{(+)}(Q)_3 Y^{(-)}$     (VI)

wherein $R_4$, Q and $Y^{(-)}$ are as defined above, or alternatively with a compound of formula (VII)

wherein $R_4$ is as defined above and $R_{11}$ is $C_1$-$C_4$ alkyl, so obtaining in both cases compounds of formula (I) wherein A is a bond; or (d) cyclopropanating a compound of formula (VIII)

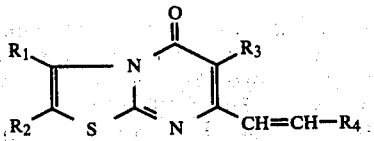

wherein $R_1$, $R_2$, $R_3$ and $R_4$ are as defined above, so obtaining compounds of formula (I) wherein A is a —$CH_2$— group; and, if desired, converting a compound of formula (I) into another compound of formula (I) and/or if desired, converting a compound of formula (I) into pharmaceutically acceptable salt thereof and/or, if desired, converting a salt into a free compound and/or, if desired, separating a mixture of isomers into the single isomers.

The acidic anion $Y^{(-)}$ in the compounds of formula (IV) and (VI) is, for example, an acidic anion derived from a hydrohalic acid, preferably derived from hydrochloric or hydrobromic acid.

When Q in the compounds of formula (IV) and (VI) is aryl, it is preferably phenyl; and when Q is $C_1$-$C_6$ alkyl, it is preferably ethyl.

The reaction of a compound of formula (II) or a salt thereof with an aldehyde of formula (III) is preferably carried out in the presence of a basic condensing agent such as sodium ethoxide, sodium methoxide, sodium hydride, sodium amide or sodium hydroxide, in a solvent selected, e.g., from the group consisting of methanol, ethanol, isopropanol, dioxane, water and their mixtures, at a temperature preferably ranging between about 0° C. and 120° C.

The reaction between a compound of formula (IV) and an aldehyde of formula (III) as well as the reaction of a compound of formula (V) with a compound of formula (VI) or with a compound of formula (VII), may, for example, be carried out by treatment with a base such as dimethylsulphinyl carbanion or sodium methoxide or sodium hydride or potassium terbutoxide or with an alkyl lithium derivative, preferably with methyl lithium or butyl lithium or phenyl lithium, in an organic solvent such as dichloromethane, dichloroethane, benzene, toluene, tetrahydrofuran, dimethylsulfoxide, dimethylformamide, dimethylacetamide or their mixtures at a temperature varying from about 0° C. about 100° C.

The cyclopropanation of a compound of formula (VIII) may be carried out, for example, by reaction with dimethylsulphoxonium methylide (prepared e.g. according to the method described in J. Chem. Soc., 1967, 2495), operating in an inert organic solvent selected, e.g., from the group consisting of dimethylformamide, dimethylsulfoxide, dioxane and their mixtures at a temperature ranging preferably between about 0° C. and about 50° C. Preferably 1-3 moles, in particular 1-1.5 moles, of the reagent are used for one mole of the compound of formula (VIII).

A compound of formula (I) may be converted, as stated above, into another compound of formula (I) by known methods; for example, free hydroxy groups, may be etherified by reacting with a suitable alkyl halide in the presence of a base such as NaOH, KOH, $Na_2CO_3$, NaH, $NaNH_2$, sodium methoxide, $K_2CO_3$ or sodium ethoxide, in a solvent selected from the group consisting, for example, of methanol, ethanol, dioxane, acetone, dimethylformamide, hexamethylphosphorotriamide, tetrahydrofuran, water and their mixtures at a temperature ranging preferably between about 0° C. and about 150° C.

Furthermore the etherified hydroxy groups may be converted into free hydroxy groups, for example, by treatment with pyridine hydrochloride or with a strong acid such as HCl, HBr or HI, or with a Lewis acid such as AlCl$_3$ or BBr$_3$. A compound of formula (I) wherein R$_1$ and/or R$_2$ independently is a group

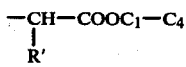

alkyl wherein R' is as defined above may be converted into a compound of formula (I) wherein R$_1$ and/or R$_2$ independently is a group

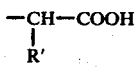

wherein R' is as defined above by hydrolysis, e.g. acid hydrolysis, using, for example, HCl, HBr, HI in water, preferably in the presence of an organic solvent such as acetic acid or dioxane, operating at a temperature varying from room temperature to about 150° C.; the same reaction may be also carried out e.g. by treatment with lithium bromide in dimethylformamide at a temperature higher than 50° C.

A compound of formula (I) wherein R$_1$ and/or R$_2$ is independently a group

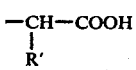

wherein R' is as defined above may be converted into another compound of formula (I) wherein R$_1$ and/or R$_2$ is independently a group of formula

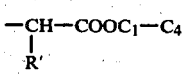

alkyl by conventional methods, for example by reacting an alkaline salt of the acid with a suitable alkyl halide in an inert solvent, such as acetone, dioxane, dimethylformamide or hexamethylphosphorotriamide at a temperature ranging from 0° C. to about 100° C.

Alternatively the esterification of a compound of formula (I) wherein R$_1$ and/or R$_2$ is independently a group

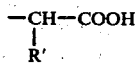

wherein R' is as defined above, may be effected by converting the carboxylic acid into the corresponding halocarbonyl, preferably chlorocarbonyl, derivate, by reaction, e.g., with the desired acid halide, for example oxalyl chloride, thionyl chloride, PCl$_3$, PCl$_5$ or POCl$_3$, either in the absence of solvents or in an inert organic solvent such as benzene, toluene, xylene, dioxane, dichloroethane, methylene chloride or tetrahydrofuran, at a temperature ranging preferably from about 0° C. to about 120° C.; and then by reacting the resulting halocarbonyl derivative with the suitable alcohol of formula R''—OH, wherein R'' is a C$_1$-C$_4$ alkyl group, in an inert solvent such as benzene, toluene, xylene, dioxane, dichloroethane, methylene chloride or tetrahydrofuran, at temperatures varying between about 0° C. and about 120° C., preferably in the presence of a base, such as, triethylamine or pyridine. A hydroxy or an amino group as substituents in a phenyl ring in a compound of formula (I) may be converted respectively into a C$_2$-C$_8$ alkanoyloxy or C$_2$-C$_8$ alkanoylamino group using conventional methods well known in organic chemistry.

A nitro group as substituent in a phenyl ring in a compound of formula (I) may be converted into an amino group by treatment, for example, with stannous chloride in concentrated hydrochloric acid, using, if necessary, an organic cosolvent such as acetic acid, dioxane, tetrahydrofuran, at a temperature varying between room temperature and about 100° C.

Also the optional salification of a compound of formula (I) as well as the conversion of a salt into the free compound and the separation of a mixture of isomers into the single isomers may be carried out by conventional methods.

For example the separation of a mixture of optical isomers into the individual isomers may be carried out by salification with an optically active base and subsequent fractional crystallization.

Thus, the separation of a mixture of geometric isomers may be carried out, for example, by fractional crystallization.

The compounds of formula (II) wherein R$_3$ is different from hydroxy and bromine may be prepared, e.g., by reacting a compound of formula (IX)

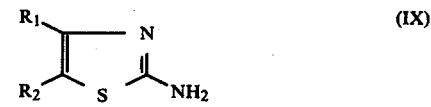 (IX)

wherein R$_1$ and R$_2$ are as defined above or a salt thereof, with a compound of formula (X)

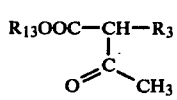 (X)

wherein R$_3$ is as defined above but is different from hydroxy and bromine and R$_{13}$ is preferably C$_1$-C$_4$ alkyl.

The reaction between a compound of formula (IX) and a compound of formula (X) may, for example, be carried out in the presence of an acid condensing agent such as polyphosphoric acid (polyphosphoric acid means a mixture of about equal weights of 99% H$_3$PO$_4$ and P$_2$O$_5$), sulphuric acid, methanesulphonic acid or p-toluenesulphonic acid, at a temperature ranging preferably between about 50° C. and 150° C.; the reaction may be carried out in an organic solvent such as, dimethylformamide, dimethylacetamide, acetic acid, formic acid, benzene, toluene, xylene, ethylene glycol monomethylether, dichloroethane, or in the absence of a solvent. Alternatively the compounds of formula (II) wherein R$_3$ is alkoxy or alkenyloxy may, for example, be prepared by reacting a compound of formula (XI)

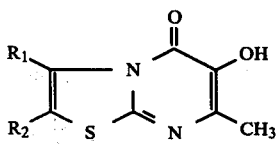

(XI)

wherein $R_1$ and $R_2$ are as defined above, with a suitable $C_1$–$C_4$ alkyl or $C_3$–$C_4$ alkenyl halide, preferably chloride, bromide or iodide, in a solvent such as acetone, dioxane, dimethylformamide in the presence of a basic agent such as sodium hydride, sodium methoxide, sodium or potassium carbonate, at a temperature ranging from the room temperature to about 120° C.

The compounds of formula (II) wherein $R_3$ is halogen, e.g., bromine or chlorine, may be obtained, for example, by reacting a compound of formula (II) wherein $R_3$ is hydrogen with a suitable halosuccinimide, e.g. N-bromosuccinimide, or with $SO_2Cl_2$, operating at a temperature ranging from 20° C. to about 100° C. in a solvent such as benzene or carbon tetrachloride, respectively.

The compounds of formula (IV) may be prepared by reacting a compound of formula (XII)

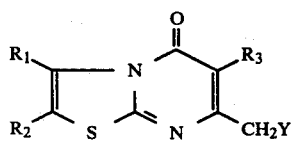

(XII)

wherein Y is a radical capable of being converted to an anion $Y^{(-)}$ as defined above and $R_1$, $R_2$ and $R_3$ are as defined above, with $P(Q)_3$, where Q is as defined above, in a solvent such as, benzene, toluene, xylene or acetonitrile at a temperature varying between room temperature and reflux temperature.

The compounds of formula (V) may be prepared for example by oxidizing a compound of formula (XIII)

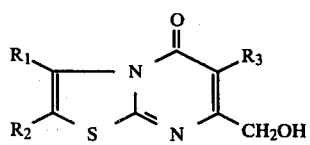

(XIII)

wherein $R_1$, $R_2$ and $R_3$ are as defined above, for example, with dimethylsulfoxide in the presence of dicyclohexylcaarbodiimide and phosphoric acid or pyridinium-trifluoroacetate (Moffat reaction) in a solvent such a benzene, toluene or dimethylsulfoxide at a temperature varying between 0° C. and 50° C.

Alternatively the compounds of formula (V) may be prepared for example, by hydrolysing a compound of formula (XIV)

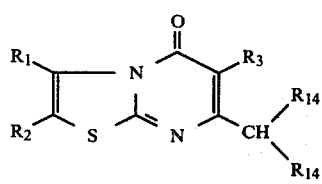

(XIV)

wherein $R_1$, $R_2$ and $R_3$ are as defined above and $R_{14}$ represents halogen, in particular chlorine or bromine, or a $C_1$–$C_6$ alkoxy group: the hydrolysis of a compound of formula (XIV) may be carried out, for example, by treatment with an aqueous mineral acid such as HCl, HBr, HI, $H_2SO_4$ preferably in the presence of a solvent such as methanol, ethanol, acetone, dioxane, tetrahydrofuran at a temperature varying from the room temperature to about 120° C. The compounds of formula (VIII) may be prepared, for example, by reacting a compound of formula (II) with an aldehyde of formula (III), using the same experimental conditions as defined above.

The compounds of formula (XI) may be prepared, for example, by hydrolyzing a compound of formula (XV)

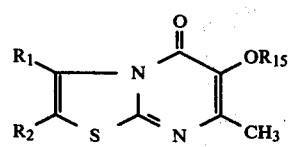

(XV)

wherein $R_1$ and $R_2$ are as defined above and $R_{15}$ represents formyl or a $C_2$–$C_8$ alkanoyl group: the hydrolysis may be carried out, for example, by treatment with a base such as $NaHCO_3$, $KHCO_3$, $Na_2CO_3$, $K_2CO_3$, NaOH, KOH or with a mineral acid such as HCl, HBr, HI, $H_2SO_4$, $H_3PO_4$, in aqueous medium or in the presence of an organic cosolvent as dioxane, acetone, methanol, ethanol, tetrahydrofuran, dimethylformamide, at a temperature varying between room temperature an the reflux temperature.

The compounds of formula (XII) wherein Y is halogen and $R_3$ is hydrogen may, for example, be prepared by reacting a compound of formula (IX) or a salt thereof, with a compound of formula (XVI)

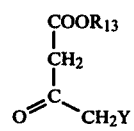

(XVI)

wherein $R_{13}$ is as defined above and Y represents a halogen atom, preferably chlorine, using the same experimental conditions as defined above for the reaction between a compound of formula (IX) and a compound of formula (X).

The compounds of formula (XII) wherein $R_3$ is different from hydrogen, and Y is halogen, e.g., chlorine or bromine, may be prepared, for example, from a compound of formula (II), wherein $R_3$ is different from hydrogen, by reaction with a N-halo-succinimide, preferably N-bromosuccinimide, in a solvent such as benzene or $CCl_4$ at a temperature varying between room temperature and the reflux temperature. Alternatively the compounds of formula (XII) wherein $R_3$ is chlorine or bromine may be prepared by reacting a compound of formula (XII) wherein $R_3$ is hydrogen with a suitable halogenating agent such as chlorosuccinimide or bromosuccinimide, $SO_2Cl_2$ or pyridinium bromide perbromide, operating at a temperature ranging from 0° C. to 100° C. and using, for example, as solvent $CCl_4$ or dichloroethane in the reaction with $SO_2Cl_2$; pyridine in the reaction with pyridinium bromide perbromide and benzene in the reaction with an halosuccinimide.

The compounds of formula (XIII) may be prepared, for example, by reacting a compound of formula (XII)

wherein Y is a good leaving group, for example, Cl or Br, with potassium or sodium acetate in dimethylformamide at a temperature varying between room temperature and 100° C., so obtaining the correspondining acetoxy-derivative, which in turn is hydrolysed to the corresponding alcohol (XIII), for example, by treatment with 37% HCl in dioxane at a temperature varying between room temperature and the reflux temperature.

The compounds of formula (XIV) may be prepared, for example, by reacting a compound of formula (IX) with a compound of formula (XVII)

(XVII)

wherein $R_3$, $R_{13}$ and $R_{14}$ are as defined above and $R_{16}$ represents amino, $C_1$-$C_6$ alkoxy or tri($C_1$-$C_6$)alkylsilyloxy, by heating in an inert solvent such as dioxane, toluene, xylene, dimethylformamide, dimethylacetamide or in the absence of a solvent at a temperature varying from about 50° C. to about 170° C., preferably from about 120° C. to about 150° C.

The compounds of formula (XV) may be prepared by reacting a compound of formula (IX) or a salt thereof with a compound of formula (XVIII)

(XVIII)

wherein $R_{13}$ and $R_{15}$ are as defined above.

The reaction between a compound of formula (IX) and a compound of formula (XVIII) may, for example, be carried out in the presence of an acid condensing agent such as polyphosphoric acid (polyphosphoric acid means a mixture of about equal weights of 99% $H_3PO_4$ and $P_2O_5$), sulphuric acid, methanesulphonic acid or p-toluenesulphonic acid, at a temperature ranging preferably between about 50° C. and 150° C.; the reaction is preferably carried out in an organic solvent such as dimethylformamide, dimethylacetamide, benzene, toluene, xylene, ethylene glycol monomethylether or dichloroethane, but it may be also carried out in the absence of a solvent.

The compounds of formula (III), (VI), (VII), (IX), (X), (XVI) and (XVII) are known compounds and may be prepared by conventional methods: in some cases they are commercially available products.

The compounds of the present invention are active on the gastroenteric system, in particular they are endowed with anti-ulcerogenic and gastric anti-secretory activity and are therefore useful in therapy, for example in the prevention and treatment of peptic, e.g. duodenal, gastric and esophageal, ulcers and to inhibit gastric acid secretion. The compounds of the invention are also useful for reducing the undesiderable gastrointestinal side-effects resulting from systemic administration of anti-inflammatory prostaglandin synthetase inhibitors and may be, therefore, used for this purpose in association with them. The anti-ulcerogenic activity of the compounds of the invention is shown, e.g., by the fact that they are active in the test of the inhibition of restraint ulcers in rats, according to the method of Bonfils et al., (Thérapie, 1960, 5, 1096; Jap. J. Pharmac. 1945, 43, 5). Six Sprague-Dawley male rats (100-120 g) fasted 24 hours were used for the experiment: a square flexible small-mesh wire netting was used for the immobilization and 4 hours after the immobilization the rats were sacrificed, their stomachs were removed and the lesions counted under a dissecting microscope. The tested compounds were administered per os (p.o.) one hour before the immobilization. The following Table I shows, for example, the approximate $ED_{50}$ values of the antiulcerogenic activity obtained in the above test in the rat after oral administration for two compounds of this invention:

TABLE I

| Compound | Antiulcerogenic activity p.o. |
|---|---|
| 7-trans-[2-(3-pyridyl)-ethenyl]-5H—thiazolo[3,2-a]pyrimidine-5-one | $ED_{50}$ = 9 mg/kg |
| 2-chloro-7-trans-[2-(3-pyridyl)-ethenyl]-5H—thiazolo[3,2-a]pyrimidine-5-one | $ED_{50}$ = 10 mg/kg |

The compounds of the invention own also gastric antisecretory activity as shown, e.g., by the fact that they proved to be active, after intraduodenal administration, in inhibiting the gastric secretion in rats according to the method of H. Shay et al. (Gastroenter., 1945, 43, 5). Gastric antisecretory activity was evaluated in rats by the pylorus ligature technique. Six Sprague-Dawley male rats (110-130 g) were used for each group. Twenty-four hours before the test, the rats were deprived of food but their water supply was maintained. On the day of the operation, the pylorus was ligated under light ether anaesthesia. Each compound was injected intraduodenally (i.d.) at the time of the ligature. Four hours after the ligature the rats were sacrificed, the stomach secretion was collected and centrifuged at 3500 r.p.m. for 10 minutes, and the volume, less sediment, was determined.

The amount of the free hydrochloric acid in the gastric juice was determined by titration against 0.01 N sodium hydroxide to pH 7.0.

One of the preferred compounds of this invention having gastric antisecretory activity is, for example, the compound 6-methoxy-7-trans-[2-(3-pyridyl)-ethenyl]-5H-thiazolo[3,2-a]pyrimidine-5-one, which has an approximate $ED_{50}$ value of 30 mg/kg in the above test in the rat, after intraduodenal administration.

The compounds of this invention possess also anti-inflammatory activity as demonstrated e.g. by the fact that they are active, after oral administration, in inhibiting: (A) the edema formation in the hind paw of rats in response to a subplantar injection of carrageenin, according to the method of C. A. Winter et al. (J. Pharmac. Exp. Therap. 1963, 141, 369) and P. Lence (Arch. Int. Pharmacodyn., 1962, 136, 237), and (B) the Reversed Passive Arthus Reaction (RPAR) in rat paw, induced by the interaction of antigen and antibody resulting in the formation of precipitating immune complex, followed by fixation of complement and accumulation of polymorphonuclear leucocytes at a focal point (D. K. GEMMELL, J. COTTNEY and A. J. LEWIS, Agents and Actions 9/1 pag. 107, 1979). The compounds of this invention are also endowed with analgesic activity. The analgesic activity was assessed, for example, by means of phenylquinone induced writhing test in mice according to Siegmund [Siegmund et al. Proc. Soc. Exper. Biol. Med., 95, 729 (1957)].

Therefore the compounds of the invention may be used in therapy to treat pains and inflammatory processes, such as for example, rheumatoid arthritis and osteoarthrosis. The following Tables II and III show, for example, the approximate $ED_{25}$ values of the anti-inflammatory activity in the above tests in the rat after oral administration for some compounds of this invention:

TABLE II

| Compound | Anti-inflammatory activity Carrageenin induced oedema |
|---|---|
| 7-trans-[2-(3-pyridyl)-ethenyl]-5H—thiazolo[3,2-a]pyrimidine-5-one | $ED_{25} =$ 6 mg/kg |
| 2-chloro-7-trans-[2-(3-pyridyl)-ethenyl]-5H—thiazolo[3,2-a]pyrimidine-5-one | $ED_{25} =$ 16 mg/kg |
| 6-methoxy-7-trans-[2-(3-pyridyl)-ethenyl]-5H—thiazolo[3,2-a]pyrimidine-5-one | $ED_{25} =$ 15 mg/kg |

TABLE II

| Compound | Anti-inflammatory activity RPAR reaction |
|---|---|
| 6-methyl-7-trans-[2-(3-pyridyl)-ethenyl]-5H—thiazolo[3,2-a]pyrimidine-5-one | $ED_{25} =$ 22 mg/g |
| 2-chloro-7-trans-[2-(3-pyridyl)-ethenyl]-5H—thiazolo 8 3,2-:a]pyrimidine-5-one | $ED_{25} =$ 25 mg/g $ED_{25} =$ 25 mg/kg |

With regard to the analgesic activity, one of the preferred compounds of this invention is, for example, the compound 2-chloro-7-trans-[2-(3-pyridyl)-ethenyl]-5H-thiazolo[3,2-a]pyrimidine-5-one, wich has an approximate $ED_{25}$ value of 25 mg/kg in the phenylquinone-induced writhing test in the rat, after oral administration. Furthermore the compounds of this invention are effective in the inhibiting the $TXA_2$ synthetase in vivo and may be therefore useful in therapy, for example, in the prevention and treatment of all kinds of thrombosis, peripheral vasculopaties and coronary artery diseases.

The activity on the $TXA_2$ synthetase was evaluated, e.g., in rat by administering the compounds at a single oral dose of 10 mg/kg and determining the concentration of $TXB_2$ in the serum of the animals killed two hours after the administration of the drug.

As preferred example of compound having $TXA_2$ synthetase inhibiting activity, the following can be mentioned:

6-methyl-7-trans-[2-(3-pyridyl)-ethenyl]-5H-thiazolo[3,2-a]pyrimidine-5-one.

In view of their high therapeutic index, the compounds of the invention can be used safely in medicine. For example, the approximate acute toxicity ($LD_{50}$) of the compounds 7-trans-[2-(3-pyridyl)-ethenyl]-5H-thiazolo[3,2-a]pyrimidine-5-one and 2-chloro-7-trans-[2-(3-pyridyl)-ethenyl]-5H-thiazolo[3,2-a]pyrimidine-5-one in the mouse determined by single administration of increasing doses and measured on the seventh day of treatment, is higher than 800 mg/kg per os. Analogous toxicity data have been found for other compounds of the invention.

The compounds of the invention can be administered in a variety of dosage forms, e.g. orally, in the form of tablets, capsules, sugar or film coated tablets, liquid solutions or suspensions, rectally, in the form of suppositories, parenterally, e.g. intramuscularly, or by intravenous injection or infusion.

The dosage depends on the age, weight, conditions of the patient and administration route; for example the dosage adopted for oral administration to adult humans ranges from about 50 to about 200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsiony may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

2-amino-thiazole (3.06 g) was reacted with ethyl 2-methylacetoacetate (6.4 g) in polyphosphoric acid (15.3 g: 7.1 g of $P_2O_5$ and 8.2 g of 99% $H_3PO_4$) under stirring at 100° C. for two hours.

After cooling, dilution with ice water and neutralization, the precipitate was filtered, washed with water and crystallized from isopropyl ether to give 6,7-dimethyl-5H-thiazolo[3,2-a]pyrimidine-5-one, m.p. 112°–113° C. (5.04 g), which was reacted with 3-pyridine-carboxaldehyde (5.99 g) in methanol (130 ml) in the presence of sodium methoxide (4.55 g) under stirring at reflux temperature for 12 hours. After cooling the precipitate was filtered and washed with water until neutral: crystallization from methanol gave 3.2 g of 6-methyl-7-trans-[2-(3-pyridyl)-ethenyl]-5H-thiazolo[3,2-a]pyrimidine-5-one, m.p. 192°–194° C., NMR ($CDCl_3$) δ ppm: 2.36 (s) (3H, $CH_3$), 6.97 (d) (H, C-2 proton), 7.38 (dd) (1H, C-5 pyridyl proton), 7.38 (d) (1H, β-ethenyl proton), 7.91 (d) (1H, δ-ethenyl proton), 7.97 (d) (1H, C-3 proton), 8.00 (m) (1H, C-4 pyridyl proton), 8.62 (dd) (1H, C-6 pyridyl proton), 8.88 (d) (1H, C-2 pyridyl proton); $J_{H\alpha H\beta} = 16$ Hz.

By proceeding analogously, using the suitable aldehydes, the following compounds were prepared:
  6-methyl-7-trans-[2-(4-pyridyl)-ethenyl]-5H-thiazolo[3,2-a]pyrimidine-5-one, m.p. 252°–253° C.;
  6-methyl-7-trans-[2-(6-methyl-2-pyridyl)-ethenyl]-5H-thiazolo[3,2-a]pyrimidine-5-one, m.p. 198°–199° C.;
  6-methyl-7-trans-[2-(1-methyl-2-pyrrolyl)-ethenyl]-5H-thiazolo[3,2-a]pyrimidine-5-one;
  6-methyl-7-trans-[2-(2-pyridyl)-ethenyl]-5H-thiazolo[3,2-a]pyrimidine-5-one, m.p. 189°–190° C.;
  6-methyl-7-trans-(2-phenyl-ethenyl)-5H-thiazolo[3,2-a]pyrimidine-5-one, m.p. 173°–175° C.;
  6-methyl-7-trans-[2-(4-chloro-phenyl)-ethenyl]-5H-thiazolo[3,2-a]pyrimidine-5-one, m.p. 223°–224° C.;
  6-methyl-7-trans-[2-(2,6-dichloro-phenyl)-ethenyl]-5H-thiazolo[3,2-a]pyrimidine-5-one, m.p. 202°–204° C.;
  2-cyano-6-methyl-7-trans-[2-(3-pyridyl)-ethenyl]-5H-thiazolo[3,2-a]pyrimidine-5-one;
  6-methyl-7-trans-[2-(3-methyl-phenyl)-ethenyl]-5H-thiazolo[3,2-a]pyrimidine-5-one;
  6-methyl-7-trans-[2-(4-methyl-phenyl)-ethenyl]-5H-thiazolo[3,2-a]pyrimidine-5-one, m.p. 190°–192° C.;
  6-methyl-7-trans-[2-(2-methoxy-3-ethoxy-phenyl)-ethenyl]-5H-thiazolo[3,2-a]pyrimidine-5-one; and
  6-methyl-2-phenyl-7-trans-[2-(3-pyridyl)-ethenyl]-5H-thiazolo[3,2-a]pyrimidine-5-one, m.p. 274°–277° C.

EXAMPLE 2

By proceeding according to the example 1, using the suitable ethyl 2-alkyl-acetoacetates, the following compounds were prepared:
  6-ethyl-7-trans-[2-(3-pyridyl)-ethenyl]-5H-thiazolo[3,2-a]pyrimidine-5-one, m.p. 176°–177° C.;
  6-propyl-7-trans-[2-(3-pyridyl)-ethenyl]-5H-thiazolo[3,2-a]pyrimidine-5-one, m.p. 190°–191° C.;
  6-ethyl-7-trans-[2-(4-pyridyl)-ethenyl]-5H-thiazolo[3,2-a]pyrimidine-5-one;
  6-propyl-7-trans-[2-(2-pyridyl)-ethenyl]-5H-thiazolo[3,2-a]pyrimidine-5-one;
  6-ethyl-7-trans-[2-(2-pyridyl)-ethenyl]-5H-thiazolo[3,2-a]pyrimidine-5-one; and
  6-ethyl-7-trans-[2-(6-methyl-2-pyridyl)-ethenyl]-5H-thiazolo[3,2-a]pyrimidine-5-one.

EXAMPLE 3

By proceeding according to example 1, using ethyl 2-chloro-acetoacetate, the following compounds were prepared:
  6-chloro-7-trans-[2-(3-pyridyl)-ethenyl]-5H-thiazolo[3,2-a]pyrimidine-5-one, m.p. 235°–237° C.;
  6-chloro-7-trans-(2-phenyl-ethenyl)-5H-thiazolo[3,2-a]pyrimidine-5-one, m.p. 230°–232° C.;
  6-chloro-7-trans-[2-(4-chloro-phenyl)-ethenyl]-5H-thiazolo[3,2-a]pyrimidine-5-one, m.p. 271°–272° C.; and
  6-chloro-7-trans-[2-(2,6-dichloro-phenyl)-ethenyl]-5H-thiazolo[3,2-a]pyrimidine-5-one.

EXAMPLE 4

2-amino-thiazole (5 g) was reacted with ethyl 4-chloroacetoacetate (10.8 g) in polyphosphoric acid (25 g) under stirring at 100° C. for 8 hours.

After cooling, dilution with ice water and neutralization, the precipitate was filtered and washed with water: the obtained 7-chloromethyl-5H-thiazolo[3,2-a]pyrimidine-5-one, m.p. 136°–138° C., (8.8 g), was reacted with triphenylphosphine (12.8 g) in acetonitrile (130 ml) under stirring at reflux temperature for 30 hours. After cooling the precipitate was filtered and washed with isopropyl ether to give (5H-thiazolo[3,2-a]pyrimidine-5-one-7-yl)-methyl-triphenylphosphonium chloride, m.p. 295°–299° C., (20.6 g), which was added under stirring to a suspension of 50% NaH (2.61 g) in dimethylsulphoxide (300 ml) and dichloroethane (200 ml) and reacted with 3-pyridine-carboxaldehyde (7.15 g) at room temperature for 6 hours. After evaporation of the dichloro-ethane in vacuo the solution was diluted with ice water and the precipitate was filtered and washed with water: crystallization from isopropyl alcohol gave 6.2 g of 7-trans-[2-(3-pyridyl)-ethenyl]-5H-thiazolo[3,2-a]pyrimidine-5-one, m.p. 206°–207° C., NMR (DMSO d6) δ ppm: 6.41 (s) (1H, C-6 proton), 7.36 (d) (1H, β-ethenyl proton), 7.45 (dd) (1H, C-5 pyridyl proton), 7.58 (d) (1H, C-2 proton), 7.82 (d) (1H, α-ethenyl proton), 8.06 (d) (1H, C-3 proton), 8.17 (dt) (1H, C-4 pyridyl proton), 8.60 (dd) (1H, C-6 pyridyl proton), 8.91 (d) (1H, C-2 pyridyl proton); $J_{H\alpha H\beta} = 16$ Hz.

By proceeding analogously, using the suitable aldehydes, the following compounds were prepared:
  7-trans-[2-(2-pyridyl)-ethenyl]-5H-thiazolo[3,2-a]pyrimidine-5-one, m.p. 231°–232° C.;
  7-trans-[2-(4-pyridyl)-ethenyl]-5H-thiazolo[3,2-a]pyrimidine-5-one, m.p. 246°–247° C.;
  7-trans-[2-(6-methyl-2-pyridyl)-ethenyl]-5H-thiazolo[3,2-a]pyrimidine-5-one, m.p. 213°–216° C.;
  7-trans-[2-(2-pyrrolyl)-ethenyl]-5H-thiazolo[3,2-a]pyrimidine-5-one, m.p. 209°–211° C.;
  7-trans-[2-(1-methyl-2-pyrrolyl)-ethenyl]-5H-thiazolo[3,2-a]pyrimidine-5-one, m.p. 211°–212° C.;
  7-trans-[2-(1-ethyl-2-pyrrolyl)-ethenyl]-5H-thiazolo[3,2-a]pyrimidine-5-one;
  7-trans-(2-phenyl-ethenyl)-5H-thiazolo[3,2-a]pyrimidine-5-one, m.p. 198°–200° C.;
  7-trans-[2-(3-chloro-phenyl)-ethenyl]-5H-thiazolo[3,2-a]pyrimidine-5-one, m.p. 230°–233° C.;
  7-trans-[2-(4-chloro-phenyl)-ethenyl]-5H-thiazolo[3,2-a]pyrimidine-5-one, m.p. 208°–209° C.;

7-trans-[2-(2,6-dichloro-phenyl)-ethenyl]-5H-thiazolo[3,2-a]pyrimidine-5-one, m.p. 175°–177° C.;

7-trans-[2-(3-methoxy-phenyl)-ethenyl]-5H-thiazolo[3,2-a]pyrimidine-5-one, m.p. 185°–186° C.;

7-trans-[2-(3-hydroxy-phenyl)-ethenyl]-5H-thiazolo[3,2-a]pyrimidine-5-one, m.p. 226°–229° C.;

7-trans-[2-(4-hydroxy-3-iodo-phenyl)-ethenyl]-5H-thiazolo[3,2-a]pyrimidine-5-one, m.p. 250°–270° C. dec.;

7-trans-[2-(4-N,N-dimethylamino-phenyl)-ethenyl]-5H-thiazolo[3,2-a]pyrimidine-5-one, m.p. 233°–234° C.;

7-trans-[2-(2-nitro-phenyl)-ethenyl]-5H-thiazolo[3,2-a]pyrimidine-5-one, m.p. 280°–290° C. dec.;

7-trans-{2-[3-(3-N,N-dimethylamino)-propoxy-phenyl]-ethenyl}-5H-thiazolo[3,2-a]pyrimidine-5-one;

7-trans-[2-(4-methyl-phenyl)-ethenyl]-5H-thiazolo[3,2-a]pyrimidine-5-one, m.p. 214°–216° C.;

7-trans-[2-(3-methyl-phenyl)-ethenyl]-5H-thiazolo[3,2-a]pyrimidine-5-one; and 7-trans-[2-(2-methoxy-3-ethoxy-phenyl)-ethenyl]-5H-thiazolo[3,2-a]pyrimidine-5-one.

EXAMPLE 5

2-amino-5-chloro-thiazole hydrochloride (8 g) was reacted with ethyl-4-chloroacetoacetate (15.8 g) in polyphosphoric acid (40 g) under stirring at 110° C. for 1 hour. After cooling, dilution with water and neutralization with 35% NaOH, the precipitate was filtered and washed with water. Cristallization from isopropyl ether gave 2-chloro-7-chloromethyl-5H-thiazolo[3,2-a]pyrimidine-5-one, m.p. 123°–125° C. (7.45 g), which was reacted with triphenylphosphine (9.42 g) in acetonitrile (100 ml) under stirring at reflux temperature for 10 hours. After cooling the precipitate was filtered and washed with acetonitrile to give (2-chloro-5H-thiazolo[3,2-a]pyrimidine-5-one-7-yl)-methyl-triphenyl-phosphonium chloride, m.p. 300°–310° C. dec. (10 g) which was suspended in dimethylsulfoxide (40 ml) and treated with potassium tert-butoxide (2.48 g) dissolved in dimethylsulfoxide (40 ml) at room temperature under stirring for 10 minutes. To the solution of the ylide so obtained 3-pyridine-carboxaldehyde (2.45 g) dissolved in dimethylsulfoxide (20 ml) was added and the reaction mixture was kept under stirring at room temperature for 15 minutes: after dilution with ice water and neutralization with NaH2PO4 the precipitate was filtered and crystallized from CH2Cl2-isopropyl alcohol to give 4.3 g of 2-chloro-7-trans-[2-(3-pyridyl)-ethenyl]-5H-thiazolo[3,2-a]pyrimidine-5-one, m.p. 189°–190° C., NMR (CDCl3) δ ppm: 6.24 (s) (1H, C-6 proton), 6.91 (d) (1H, β-ethenyl proton), 7.30 (dd) (1H, C-5 pyridyl proton), 7.71 (d) (1H, α-ethenyl proton), 7.82 (s) (1H, C-3 proton), 7.87 (ddd) (1H, C-4 pyridyl proton), 8.55 (dd) (1H, C-6 pyridyl proton), 8.77 (d) (1H, C-2 pyridyl proton); $J_{H\alpha H\beta}=16$ Hz.

By proceeding analogously the following compounds were prepared:

2-chloro-7-trans-[2-(4-pyridyl)-ethenyl]-5H-thiazolo[3,2-a]pyrimidine-5-one;

2-chloro-7-trans-[2-(1-methyl-2-pyrrolyl)-ethenyl]-5H-thiazolo[3,2-a]pyrimidine-5-one;

3-methyl-7-trans-[2-(3-pyridyl)-ethenyl]-5H-thiazolo[3,2-a]pyrimidine-5-one, m.p. 191°–193° C.;

2,3-dimethyl-7-trans-[2-(3-pyridyl)-ethenyl]-5H-thiazolo[3,2-a]pyrimidine-5-one, m.p. 179°–180° C.;

3-trifluoromethyl-7-trans-[2-(3-pyridyl)-ethenyl]-5H-thiazolo[3,2-a]pyrimidine-5-one, m.p. 224°–226° C.;

2-bromo-7-trans-[2-(3-pyridyl)-ethenyl]-5H-thiazolo[3,2-a]pyrimidine-5-one, m.p. 211°–213° C.;

3-tert.butyl-7-trans-[2-(3-pyridyl)-ethenyl]-5H-thiazolo[3,2-a]pyrimidine-5-one;

2-cyano-7-trans-[2-(3-pyridyl)-ethenyl]-5H-thiazolo[3,2-a]pyrimidine-5-one, m.p. 248°–250° C., NMR (DMSO d6) δ ppm: 6.40 (s) (1H, C-6 proton), 7.32 (d) (1H, β-ethenyl proton), 7.44 (dd) (1H, C-5 pyridyl proton), 7.72 (d) (1H, α-ethenyl proton), 8.11 (ddd) (1H, C-4 pyridyl proton), 8.52 (m) (1H, C-6 pyridyl proton), 8.84 (dd) (1H, C-2 pyridyl proton), 9.00 (s) (1H, C-3 proton); $J_{H\alpha H\beta}=16$ Hz.

EXAMPLE 6

7-chloromethyl-3-phenyl-5H-thiazolo[3,2-a]pyrimidine-5-one, m.p. 194°–195° C. (7.8 g), prepared according to Example 5, was reacted with triphenylphosphine (8 g) in acetonitrile (250 ml) under stirring at the reflux temperature for 24 hours. After cooling the solution was concentrated in vacuo to a small volume, diluted with isopropyl ether and the precipitate was filtered to give 11 g of [3-phenyl-5H-thiazolo[3,2-a]pyrimidine-5-one-7-yl]-methyl-triphenylphosphonium chloride, which was suspended in dimethylsulfoxide (50 ml) and treated with potassium tert-butoxide (2.46 g) dissolved in dimethylsulfoxide (50 ml) under stirring at room temperature. The solution of the ylide so obtained was reacted with 3-pyridine-carboxaldehyde (2.36 g) at room temperature for 60 minutes then the reaction mixture was diluted with ice water and neutralized with NaH2PO4.

The precipitate was filtered and washed with water: crystallization from CH2Cl2-methanol gave 2.8 g of 3-phenyl-7-trans-[2-(3-pyridyl)-ethenyl]-5H-thiazolo[3,2-a]pyrimidine-5-one, m.p. 270°–272° C., NMR (CDCl3) δ ppm: 6.17 (s) (1H, C-6 proton), 6.70 (s) (1H, C-2 proton), 6.97 (d) (1H, β-ethenyl proton), 7.34 (dd) (1H, C-5 pyridyl proton), 6.39 (s) (5H, phenyl protons), 7.77 (d) (1H, α-ethenyl proton), 7.87 (m) (1H, C-4 pyridyl proton), 8.54 (m) (1H, C-6 pyridyl proton), 8.80 (dd) (1H, C-2 pyridyl proton); $J_{H\alpha H\beta}=16$ Hz.

By proceeding analogously the following compounds were prepared:

2-phenyl-7-trans-[2-(3-pyridyl)-ethenyl]-5H-thiazolo[3,2-a]pyrimidine-5-one;

3-(4-fluoro-phenyl)-7-trans-[2-(3-pyridyl)-ethenyl]-5H-thiazolo[3,2-a]pyrimidine-5-one, m.p. 241°–243° C.;

3-(2-chloro-phenyl)-7-trans-[2-(3-pyridyl)-ethenyl]-5H-thiazolo[3,2-a]pyrimidine-5-one;

3-(3-chloro-phenyl)-7-trans-[2-(3-pyridyl)-ethenyl]-5H-thiazolo[3,2-a]pyrimidine-5-one;

3-(4-chloro-phenyl)-7-trans-[2-(3-pyridyl)-ethenyl]-5H-thiazolo[3,2-a]pyrimidine-5-one, m.p. 282°–283° C.;

3-(3-trifluoromethyl-phenyl)-7-trans-[2-(3-pyridyl)-ethenyl]-5H-thiazolo[3,2-a]pyrimidine-5-one;

3-(2-methyl-phenyl)-7-trans-[2-(3-pyridyl)-ethenyl]-5H-thiazolo[3,2-a]pyrimidine-5-one;

3-(3-methyl-phenyl)-7-trans-[2-(3-pyridyl)-ethenyl]-5H-thiazolo[3,2-a]pyrimidine-5-one;

3-(4-methyl-phenyl)-7-trans-[2-(3-pyridyl)-ethenyl]-5H-thiazolo[3,2-a]pyrimidine-5-one, m.p. 254°–255° C.;

3-(2-methoxy-phenyl)-7-trans-[2-(3-pyridyl)-ethenyl]-5H-thiazolo[3,2-a]pyrimidine-5-one;

3-(3-methoxy-phenyl)-7-trans-[2-(3-pyridyl)-ethenyl]-5H-thiazolo[3,2-a]pyrimidine-5-one, m.p. 209°-210° C.;

3-(4-methoxy-phenyl)-7-trans-[2-(3-pyridyl)-ethenyl]-5H-thiazolo[3,2-a]pyrimidine-5-one, m.p. 241°-242° C.;

3-(2,4-dimethoxy-phenyl)-7-trans-[2-(3-pyridyl)-ethenyl]-5-thiazolo[3,2-a]pyrimidine-5-one;

3-(3,4-dimethoxy-phenyl)-7-trans-[2-(3-pyridyl)-ethenyl]-5H-thiazolo[3,2-a]pyrimidine-5-one;

3-(3,4-ethylenedioxy-phenyl)-7-trans-[2-(3-pyridyl)-ethenyl]-5H-thiazolo[3,2-a]pyrimidine-5-one, m.p. 232°-236° C.;

3-(3,4-methylenedioxy-phenyl)-7-trans-[2-(3-pyridyl)-ethenyl]-5H-thiazolo[3,2-a]pyrimidine-5-one;

3-(3,4-dihydroxy-phenyl)-7-trans-[2-(3-pyridyl)-ethenyl]-5H-thiazolo[3,2-a]pyrimidine-5-one;

3-(4-hydroxy-phenyl)-7-trans-[2-(3-pyridyl)-ethenyl]-5H-thiazolo[3,2-a]pyrimidine-5-one;

2-methyl-3-phenyl-7-trans-[2-(3-pyridyl)-ethenyl]-5H-thiazolo[3,2-a]pyrimidine-5-one, m.p. 234°-237° C.;

2-ethyl-3-phenyl-7-trans-[2-(3-pyridyl)-ethenyl]-5H-thiazolo[3,2-a]pyrimidine-5-one;

3-(4-biphenylyl)-7-trans-[2-(3-pyridyl)-ethenyl]-5H-thiazolo[3,2-a]pyrimidine-5-one, m.p. 239°-240° C.;

3-(2-naphtyl)-7-trans-[2-(3-pyridyl)-ethenyl]-5H-thiazolo[3,2-a]pyrimidine-5-one, m.p. 308°-310° C.;

3-(3-hydroxy-phenyl)-7-trans-[2-(3-pyridyl)-ethenyl]-5H-thiazolo[3,2-a]pyrimidine-5-one;

4-(4-acetoxy-phenyl)-7-trans-[2-(3-pyridyl)-ethenyl]-5H-thiazolo[3,2-a]pyrimidine-5-one;

3-(2-nitro-phenyl)-7-trans-[2-(3-pyridyl)-ethenyl]-5H-thiazolo[3,2-a]pyrimidine-5-one, m.p. 264°-266° C.;

3-(4-nitro-phenyl)-7-trans-[2-(3-pyridyl)-ethenyl]-5H-thiazolo[3,2-a]pyrimidine-5-one, m.p. 290°-293° C. (dec);

3-(2-amino-phenyl)-7-trans-[2-(3-pyridyl)-ethenyl]-5H-thiazolo[3,2-a]pyrimidine-5-one;

3-(3-amino-phenyl)-7-trans-[2-(3-pyridyl)-ethenyl]-5H-thiazolo[3,2-a]pyrimidine-5-one;

3-(4-amino-phenyl)-7-trans-[2-(3-pyridyl)-ethenyl]-5H-thiazolo[3,2-a]pyrimidine-5-one, m.p. 282°-284° C. (dec); and 2,3-diphenyl-7-trans-[2-(3-pyridyl)-ethenyl]-5H-thiazolo[3,2-a]pyrimidine-5-one, m.p. 249°-250° C.

EXAMPLE 7

7-chloromethyl-3-(3-pyridyl)-5H-thiazolo[3,2-a]pyrimidine-5-one, m.p. 280°-290° C. dec. (5.30 g), prepared according to Example 6, was reacted with triphenylphosphine (5 g) in acetonitrile (500 ml) under stirring at the reflux temperature for 40 hours. After cooling the solution was concentrated in vacuo to a small volume, diluted with isopropyl ether and the precipitate was filtered to give 8 g of [3-(3-pyridyl)-5H-thiazolo[3,2-a]pyrimidine-5-one-7-yl]methyl-triphenyl-phosphonium chloride, which was suspended in dimethylsulfoxide (100 ml) and treated with potassium tert-butoxide (1.66 g) dissolved in dimethylsulfoxide (50 ml) under stirring at room temperature. The solution of the ylide so obtained was reacted with 3-pyridine-carboxaldehyde (1.74 g) at room temperature for 30 minutes then the reaction mixture was diluted with ice water and neutralized with NaH2PO4.

The precipitate was filtered and washed with water: crystallization from CH2Cl2-methanol gave 2.8 g of 3-(3-pyridyl)-7-trans-[2-(3-pyridyl)-ethenyl]-5H-thiazolo[3,2-a]pyrimidine-5-one, m.p. 270°-272° C. NMR (CF3COOD+CDCl3) δ ppm: 6.82 (s) (1H, C-6 proton), 7.51 (d) (1H, β-ethenyl proton), 7.76 (s) (1H, C-2 proton), 7.96 (d) (1H, α-ethenyl proton), 8.01-8.36 (m) (2H, C-5 pyridyl protons), 8.70-9.00 (m) (4H, C-4 and C-6 pyridyl protons), 9.11 (bs) (2H, C-2 pyridyl protons); $J_{H\alpha H\beta} = 16$ Hz.

By proceeding analogously the following compounds were prepared:

7-trans-[2-(3-pyridyl)-ethenyl]-3-(2-thienyl)-5H-thiazolo[3,2-a]pyrimidine-5-one, m.p. 121°-125° C.;

3-(2-pyridyl)-7-trans-[2-(3-pyridyl)-ethenyl]-5H-thiazolo[3,2-a]pyrimidine-5-one; and 3-(4-pyridyl)-7-trans-[2-(3-pyridyl)-ethenyl]-5H-thiazolo[3,2-a]pyrimidine-5-one.

EXAMPLE 8

2-amino-5-chloro-thiazole hydrochloride (8 g) was reacted with ethyl-4-chloroacetoacetate (15.8 g) in polyphosphoric acid (40 g) under stirring at 110° C. for 1 hour. After cooling, dilution with water and neutralization with 35% NaOH, the precipitate was filtered and washed with water. Crystallization from isopropyl ether gave 2-chloro-7-chloromethyl-5H-thiazolo[3,2-a]pyrimidine-5-one, m.p. 123°-125° C. (7.45 g), which was reacted with triphenylphosphine (9.42 g) in acetonitrile (100 ml) under stirring at reflux temperature for 10 hours. After cooling the precipitate was filtered and washed with acetonitrile to give (2-chloro-5H-thiazolo[3,2-a]pyrimidine-5-one-7-yl)-methyl-triphenyl-phosphonium chloride, m.p. 300°-310° C. dec. (10 g) which was suspended in dimethylsulfoxide (40 ml) and treated with potassium tert-butoxide (2.48 g) dissolved in dimethylsulfoxide (40 ml) at room temperature under stirring for 10 minutes. To the solution of the ylide so obtained 5-formyl-2-methyl-thiazole (3.1 g) dissolved in dimethylsulfoxide (20 ml) was added and the reaction mixture was kept under stirring at room temperature for 15 minutes: after dilution with ice water and neutralization with NaH2PO4 the precipitate was filtered and crystallized from CH2Cl2-methanol to give 3.4 g of 2-chloro-7-trans-[2-(2-methyl-5-thiazolyl)-ethenyl]-5H-thiazolo[3,2-a]pyrimidine-5-one, m.p. 224°-226° C., NMR (CDCl3) δ ppm: 2.97 (s) (3H, —CH3), 6.61 (s) (1H, C-6 proton), 6.78 (d) (1H, β-ethenyl proton), 7.82 (d) (1H, α-ethenyl proton), 7.88 (s) (1H, C-3 proton), 8.02 (s) (1H, C-4 thiazolyl proton); $J_{H\alpha H\beta} = 16$ Hz.

By proceeding analogously, starting from suitable 2-amino-thiazoles, the following compounds were prepared:

7-trans-[2-(2-methyl-5-thiazolyl)-ethenyl]-5H-thiazolo[3,2-a]pyrimidine-5-one, m.p. 245°-248° C.;

2-cyano-7-trans-[2-(2-methyl-5-thiazolyl)-ethenyl]-5H-thiazolo[3,2-a]pyrimidine-5-one;

2,3-dimethyl-7-trans-[2-(2-methyl-5-thiazolyl)-ethenyl]-5H-thiazolo[3,2-a]pyrimidine-5-one;

2,3-diphenyl-7-trans-[2-(2-methyl-5-thiazolyl)-ethenyl]-5H-thiazolo[3,2-a]pyrimidine-5-one;

7-trans-[2-(2-methyl-5-thiazolyl)-ethenyl]-3-phenyl-5H-thiazolo[3,2-a]pyrimidine-5-one;

7-trans-[2-(2-methyl-5-thiazolyl)-ethenyl]-3-trifluoromethyl-5H-thiazolo[3,2-a]pyrimidine-5-one; and 7-trans-[2-(2-methyl-5-thiazolyl)-ethenyl]-3-(3-pyridyl)-5H-thiazolo[3,2-a]pyrimidine-5-one.

EXAMPLE 9

7-chloromethyl-5H-thiazolo[3,2-a]pyrimidine-5-one (10 g), prepared according to Example 4, was dissolved in dimethylformamide (200 ml) and reacted with anhydrous potassium acetate (10 g) under stirring at room temperature for 20 hours.

After dilution with ice water the precipitate was filtered and washed with water: crystallization from methanol gave 7-acetoxymethyl-5H-thiazolo[3,2-a]pyrimidine-5-one, m.p. 144°–145° C., (7.5 g), which was hydrolysed by treatment with 37% HCl (50 ml) in dioxane (100 ml) under stirring at room temperature for 1 hour.

The reaction mixture was diluted with acetone and the precipitate was filtered and then treated with aqueous $Na_2HPO_4$: filtration and washings with water until neutral gave 7-hydroxymethyl-5H-thiazolo[3,2-a]pyrimidine-5-one, m.p. 189°–191° C., (4.8 g), which was reacted with dicyclohexylcarbodiimide (12.6 g) in benzene (80 ml) and dimethylsulphoxide (36 ml) in the presence of trifluoroacetic acid (0.9 ml) and pyridine (1.53 ml) under stirring at room temperature for 24 hours. After treatment with oxalic acid bihydrate (2.8 g) at room temperature, the precipitate of dicyclohexylurea was filtered off and the organic solution was concentrated in vacuo to dryness: the residue was purified over a $SiO_2$ column using chloroform-ethyl acetate 8:2 as eluent. Crystallization from ethyl acetate gave 7-formyl-5H-thiazolo[3,2-a]pyrimidine-5-one, m.p. 184°–186° C., (1.3 g), which was reacted with triphenylphosphonium-benzyl chloride (1.87 g) under treatment with 50% NaH (0.274 g) in dimethylsulphoxide (6 ml) and dichloroethane (4 ml) at room temperature for 16 hours. After evaporation of solvent in vacuo, the solution was diluted with ice water and the precipitate was filtered and washed with water: crystallization from isopropyl ether gave 1.2 g of 7-trans-(2-phenyl-ethenyl)-5H-thiazolo[3,2-a]pyrimidine-5-one, m.p. 198°–200° C., NMR (DMSO d6) δ ppm: 6.40 (s) (1H, C-6 proton), 7.22 (d) (1H, β-ethenyl proton), 7.3–7.8 (m) (5H, phenyl protons), 7.54 (d) (1H, C-2-proton), 7.80 (d) (1H, α-ethenyl proton), 8.04 (d) (1H, C-3 proton); $J_{H\alpha H\beta}=16$ Hz.

EXAMPLE 10

2-amino-4,5-dimethyl-thiazole (2 g) was reacted with ethyl 3-amino-4,4-diethoxy-2-methyl-crotonate (5.4 g) in dimethylacetamide (15 ml) under stirring at 140° C. for 15 hours. After cooling the reaction mixture was diluted with ice water and extracted with ethyl acetate: the organic phase was washed with N/10 HCl and water and then decolorized with charcoal.

After evaporation in vacuo to dryness, the residue was purified over a flash column using hexane-ethyl acetate 3:2 as eluent, so obtaining 0.9 g of 7-diethoxymethyl-2,3,6-trimethyl-5H-thiazolo[3,2-a]pyrimidine-5-one, m.p. 84°–85° C., which was dissolved in dioxane (10 ml) and treated with 5% HCl (15 ml) under stirring at 50° C. for 30 minutes. After cooling the solution was neutralized with 10% NaOH, diluted with ice water and extracted with ethyl acetate: the organic solution was evaporated to dryness in vacuo and the residue was crystallized from hexane to give 0.6 g of 7-formyl-2,3-6-trimethyl-5H-thiazolo[3,2-a]pyrimidine-5-one, m.p. 170°–173° C., which was reacted at room temperature for 1 hour with the ylide obtained by treatment of (3-pyridyl)-methyl-triphenylphosphonium chloride (1.05 g) with potassium tert-butoxide (0.3 g) in dimethylsulfoxide (30 ml).

The reaction mixture was diluted with ice water containing $NaH_2PO_4$ then it was extracted with ethyl acetate: the organic solution was evaporated in vacuo to dryness and the residue was crystallized from isopropyl alcohol-hexane to give 0.25 g of 2,3,6-trimethyl-7-trans-[2-(3-pyridyl)-ethenyl]-5H-thiazolo[3,2-a]pyrimidine-5-one, m.p. 193°–195° C., NMR (CDCl$_3$) δ ppm: 2.22 (s) (3H, CH$_3$), 2.24 (s) (3H, CH$_3$), 2.70 (s) (3H, CH$_3$), 7.22 (d) (1H, β-ethenyl proton), 7.28 (ddd) (1H, C-5 pyridyl proton), 7.74 (d) (1H, α-ethenyl proton), 7.86 (ddd) (1H, C-4 pyridyl proton), 8.49 (d) (1H, C-6-pyridyl proton), 8.75 (dd) (1H, C-2 pyridyl proton); $J_{H\alpha H\beta}=16$ Hz.

By proceeding analogously the following compounds were prepared:

2-chloro-6-methyl-7-trans-[2-(3-pyridyl)-ethenyl]-5H-thiazolo[3,2-a]pyrimidine-5-one, NMR (CDCl$_3$) δ ppm: 2.28 (s) (3H, CH$_3$), 6.94 (d) (1H, β-ethenyl proton), 7.19 (dd) (1H, C-5 pyridyl proton), 7.80 (s) (1H, C-3 proton), 7.75 (d) (1H, α-ethenyl proton), 7.78 (bd) (1H, C-4 pyridyl proton), 8.56 (m) (1H, C-6 pyridyl proton), 8.77 (d) (1H, C-2 pyridyl proton); $J_{H\alpha H\beta}=16$ Hz;

3,6-dimethyl-7-trans-[2-(3-pyridyl)-ethenyl]-5H-thiazolo[3,2-a]pyrimidine-5-one, m.p. 211°–214° C.;

NMR (CDCl$_3$) δ p.p.m.: 2.24 (s) (3H, C-6 methyl), 2.80 (d) (3H, C-3 methyl), 6.30 (q) (1H, C-2 proton), 7.24 (d) (1H, β-ethenyl proton), 7.29 (dd) (1H, C-5 pyridyl proton), 7.78 (d) (1H, α-ethenyl proton), 7.85 (ddd) (1H, C-4 pyridyl proton), 8.51 (dd) (1H, C-6 pyridyl proton), 8.77 (d) (1H, C-2 pyridyl proton); $J_{H\alpha H\beta}=16$ Hz.

EXAMPLE 11

2-amino-thiazole (10 g) was reacted with ethyl 2-acetoxy-acetoacetate (37.5 g) in dimethylacetamide (375 ml) containing polyphosphoric acid (71.5 g: 42.5 g of $P_2O_5$ and 29 g of $H_3PO_4$) under stirring at 100° C. for 24 hours. After cooling, dilution with ice water and neutralization with $Na_2HPO_4$, the precipitate was extracted with ethyl acetate: the organic solution was evaporated in vacuo to dryness and the residue was purified over a $SiO_2$ column using $CHCl_3$ as eluent.

Crystallization from isopropyl ether gave 8 g of 6-acetoxy-7-methyl-5H-thiazolo[3,2-a]pyrimidine-5-one, m.p. 118°–119° C., which was hydrolyzed by treatment with $NaHCO_3$ (16 g) in methanol (80 ml) under stirring at 60° C. for 4 hours. After cooling the solution was evaporated in vacuo to a small volume and the residue was dissolved in ethyl acetate and then repeatedly extracted with aqueous NaOH.

The aqueous phase was neutralized with 37% HCl and the precipitate was extracted with chloroform: the organic solution was evaporated in vacuo to dryness. Crystallization from ethyl acetate gave 5.3 g of 6-hydroxy-7-methyl-5H-thiazolo[3,2-a]pyrimidine-5-one, m.p. 225°–227° C., which was dissolved in dimethylformamide (50 ml) and reacted with methyl iodide (8.3 g) in the presence of anhydrous $K_2CO_3$ (8.1 g) under stirring at room temperature for 16 hours. The reaction mixture was diluted with ice water and extracted with ethyl acetate then the organic solution was treated with gaseous HCl. The precipitate was filtered and washed with ethyl acetate: 6-methoxy-7-methyl-5H-thiazolo[3,2-a]pyrimidine-5-one hydrochloride, m.p. 185°–195° C. dec. (4.7 g) was obtained, which was reacted with 3-pyridyl-carboxaldehyde (5.4 g) in methanol (140 ml) in the presence of sodium methoxide (3.3 g) under stirring at reflux temperature for 24 hours. After concentration in vacuo to a small volume and dilution with isopropyl ether, the precipitate was filtered and washed with isopropyl ether and then with water. Crystallization from 50% ethanol gave 3.2 g of 6-methoxy-7-trans-[2-(3-pyridyl)-ethenyl]-5H-thiazolo[3,2-a]pyrimidine-5-one, m.p. 186°-187° C., NMR (CDCl₃) δ ppm: 4.02 (s) (3H, —OCH₃), 6.96 (d) (1H, C-2 proton), 7.32 (dd) (1H, C-5 pyridyl proton), 7.50 (d) (1H, β-ethenyl proton), 7.80 (d) (1H, α-ethenyl proton), 7.89 (d) (1H, C-3 proton), 7.96 (dt) (1H, C-4 pyridyl proton), 8.53 (dd) (1H, C-6 pyridyl proton), 8.81 (bs) (1H, C-2 pyridyl proton); $J_{H\alpha H\beta}=16$ Hz.

By proceeding analogoulsy, using suitable aryl or heteroaryl aldehydes, the following compounds were prepared:

6-methoxy-7-trans-[2-(2-pyridyl)-ethenyl]-5H-thiazolo [3,2-a]pyrimidine-5-one;

6-methoxy-7-trans-[2-(6-methyl-2-pyridyl)-ethenyl]-5H-thiazolo[3,2-a]pyrimidine-5-one;

6-hydroxy-7-trans-[2-(3-pyridyl)-ethenyl]-5H-thiazolo [3,2-a]pyrimidine-5-one;

6-ethoxy-7-trans-[2-(3-pyridyl)-ethenyl]-5H-thiazolo [3,2-a]pyrimidine-5-one, m.p. 163°-165° C.;

6-methoxy-7-trans-[2-(4-pyridyl)-ethenyl]-5H-thiazolo [3,2-a]pyrimidine-5-one;

6-methoxy-7-trans-(2-phenyl-ethenyl)-5H-thiazolo[3,2-a]pyrimidine-5-one;

6-methoxy-7-trans-[2-(2,6-dichloro-phenyl)-ethenyl]-5H-thiazolo[3,2-a]pyrimidine-5-one; and 6-propoxy-7-trans-[2-(3-pyridyl)-ethenyl]-5H-thiazolo [3,2-a]pyrimidine-5-one.

EXAMPLE 12

2-amino-5-chloro-thiazole hydrochloride (10 g) was reacted with ethyl 2-acetoxy-acetoacetate (22 g) in dimethylacetamide (400 ml) containing polyphosphoric acid (71 g: 29 g of H₃PO₄ and 42 g of P₂O₅) under stirring at 100° C. for 6 hours. After cooling, dilution with ice water and neutralization with 37% NaOH, the precipitate was extracted with ethyl acetate and the organic solution was evaporated in vacuo to dryness. The residue was hydrolyzed by treatment with 35% HCl (50 ml) in dioxane (100 ml) at reflux temperature for 2 hours: after cooling the reaction mixture was diluted with ice water and neutralized with 37% NaOH and the precipitate was extracted with ethyl acetate. The organic solution was evaporated in vacuo to dryness and the residue was crystallized from methanol to give 5.85 g of 2-chloro-6-hydroxy-7-methyl-5H-thiazolo[3,2-a]pyrimidine-5-one, m.p. 214°-217° C., which was dissolved in dimethylformamide (100 ml) and reacted with methyl iodide (15.4 g) in the presence of anhydrous K₂CO₃ (15 g) under stirring at 60° C. for 3 hours. After cooling the reaction mixture was diluted in ice water and neutralized with NaH₂PO₄: the precipitate was filtered and the aqueous phase was extracted with ethyl acetate for the complete recovering of the product. On the whole it was obtained 5.1 g of 2-chloro-6-methoxy-7-methyl-5H-thiazolo[3,2-a]pyrimidine-5-one, m.p. 138°-141° C., which was reacted with N-bromosuccinimide (17 g, added portionwise) in benzene (150 ml) at the reflux temperature for 40 hours. After cooling the reaction mixture was diluted with ethyl acetate and treated with aqueous NaHCO₃ and then with water: the separated organic solution was evaporated in vacuo to dryness and the residue was crystallized from ethyl acetate to give 2.8 g of 7-bromomethyl-2-chloro-6-methoxy-5H-thiazolo[3,2-a]pyrimidine-5-one, m.p. 160°-162° C., which was reacted with triphenylphosphine (2.6 g) in acetonitrile (50 ml ) at the reflux temperature for 3 hours. After cooling and evaporation in vacuo of the solvent, the residue was purified with ethyl acetate to give 3.8 g of (2-chloro-6-methoxy-5H-thiazolo[3,2-a]pyrimidine-5-one-7-yl)-methyl-triphenylphosphonium bromide, which was suspended in dimethylsulfoxide (45 ml) and treated with potassium tert-butoxide (0.75 g) dissolved in dimethylsulfoxide (20 ml) at room temperature under stirring for 10 minutes.

The solution of the ylide so obtained was reacted with 3-pyridine-carboxaldehyde (0.94 g) at room temperature for 1 hour. The reaction mixture was diluted with ice water, neutralized with NaH₂PO₄ and the precipitate was filtered: crystallization from ethanol gave 0.96 g of 2-chloro-6-methoxy-7-trans-[2-(3-pyridyl)-ethenyl]-5H-thiazolo[3,2-a]pyrimidine-5-one, m.p. 205°-207° C., NMR (CDCl₃—CF₃COOD) δ ppm: 3.99 (s) (3H, OCH₃), 7.69 (d) (1H, β-ethenyl proton), 7.93 (d) (1H, α-ethenyl proton), 7.99 (s) (1H, C-3 proton), 8.08 (m) (1H, C-5 pyridyl proton), 8.75 (m) (2H, C-4 and C-6 pyridyl protons), 9.02 (bs) (1H, C-2 pyridyl proton); $J_{H\alpha H\beta}=16$ Hz.

By proceeding analogously the following compounds were prepared:

6-methoxy-7-trans-[2-(2-methyl-5-thiazolyl)-ethenyl]-5H-thiazolo[3,2-a]pyrimidine-5-one;

2-chloro-6-ethoxy-7-trans-[2-(3-pyridyl)-ethenyl]-5H-thiazol[3,2-a]pyrimidine-5-one;

6-methoxy-7-trans-[2-(1-methyl-2-pyrrolyl)-ethenyl]-5H-thiazolo[3,2-a]pyrimidine-5-one;

6-methoxy-3-(2-thienyl)-7-trans-[2-(3-pyridyl)-ethenyl]-5H-thiazolo[3,2-a]pyrimidine-5-one;

2-chloro-6-methoxy-7-trans-[2-(2-methyl-5-thiazolyl)-ethenyl]-5H-thiazolo[3,2-a]pyrimidine-5-one, m.p. 225°-227° C., NMR (CDCl₃) δ ppm: 2.71 (s) (3H, —CH₃), 3.98 (s) (3H, OCH₃), 7.02 (d) (1H, β-ethenyl proton), 7.68 (s) (1H, C-4 thiazolyl proton), 7.76 (s) (1H, C-3 proton), 7.81 (d) (1H, α-ethenyl proton); $J_{H\alpha H\beta}=16$ Hz.

6-methoxy-3-trifluoromethyl-7-trans-[2-(3-pyridyl)-ethenyl]-5H-thiazolo[3,2-a]pyrimidine-5-one;

6-methoxy-3-(3-pyridyl)-7-trans-[2-(3-pyridyl)-ethenyl]-5H-thiazolo[3,2-a]pyrimidine-5-one;

6-methoxy-3-(2-pyridyl)-7-trans-[2-(3-pyridyl)-ethenyl]-5H-thiazolo[3,2-a]pyrimidine-5-one;

6-methoxy-3-(4-pyridyl)-7-trans-[2-(3-pyridyl)-ethenyl]-5H-thiazolo[3,2-a]pyrimidine-5-one;

6-methoxy-3-(4-biphenylyl)-7-trans-[2-(3-pyridyl)-ethenyl]-5H-thiazolo[3,2-a]pyrimidine-5-one;

3-methyl-6-methoxy-7-trans-[2-(3-pyridyl)-ethenyl]-5H-thiazolo[3,2-a]pyrimidine-5-one;

2,3-dimethyl-6-methoxy-7-trans-[2-(3-pyridyl)-ethenyl]-5H-thiazolo[3,2-a]pyrimidine-5-one;

6-methoxy-3-(3-methoxy-phenyl)-7-trans-[2-(3-pyridyl)-ethenyl]-5H-thiazolo[3,2-a]pyrimidine-5-one;

6-methoxy-3-(4-methoxy-phenyl)-7-trans-[2-(3-pyridyl)-ethenyl]-5H-thiazolo[3,2-a]pyrimidine-5-one;

6-methoxy-3-(4-chloro-phenyl)-7-trans-[2-(3-pyridyl)-ethenyl]-5H-thiazolo[3,2-a]pyrimidine-5-one;

6-methoxy-3-(4-methyl-phenyl)-7-trans-[2-(3-pyridyl)-ethenyl]-5H-thiazolo[3,2-a]pyrimidine-5-one; and 6-methoxy-3-phenyl-7-trans-[2-(3-pyridyl)-ethenyl]-
5H-thiazolo[3,2-a]pyrimidine-5-one.

EXAMPLE 13

By proceeding according to Example 12, using ethyl 2-methyl-acetoacetate, the following compounds were prepared:

6-methyl-3-trifluoromethyl-7-trans-[2-(3-pyridyl)-ethenyl]-5H-thiazolo[3,2-a]pyrimidine-5-one;
6-methyl-3-(3-pyridyl)-7-trans-[2-(3-pyridyl)-ethenyl]-5H-thiazolo[3,2-a]pyrimidine-5-one;
6-methyl-3-(2-pyridyl)-7-trans-[2-(3-pyridyl)-ethenyl]-5H-thiazolo[3,2-a]pyrimidine-5-one;
6-methyl-3-(4-pyridyl)-7-trans-[2-(3-pyridyl)-ethenyl]-5H-thiazolo[3,2-a]pyrimidine-5-one;
6-methyl-3-(4-biphenylyl)-7-trans-[2-(3-pyridyl)-ethenyl]-5H-thiazolo[3,2-a]pyrimidine-5-one;
2-chloro-6-methyl-7-trans-[2-(3-pyridyl)-ethenyl]-5H-thiazolo[3,2-a]pyrimidine-5-one;
6-methyl-3-phenyl-7-trans-[2-(3-pyridyl)-ethenyl]-5H-thiazolo[3,2-a]pyrimidine-5-one;
6-methyl-3-(4-chloro-phenyl)-7-trans-[2-(3-pyridyl)-ethenyl]-5H-thiazolo[3,2-a]pyrimidine-5-one;
6-methyl-3-(4-methyl-phenyl)-7-trans-[2-(3-pyridyl)-ethenyl]-5H-thiazolo[3,2-a]pyrimidine-5-one;
6-methyl-3-(4-methoxy-phenyl)-7-trans-[2-(3-pyridyl)-ethenyl[-5H-thiazolo[3,2-a]pyrimidine-5-one; and
6-methyl-3-(2-thienyl)-7-trans-[2-(3-pyridyl)-ethenyl]-5H-thiazolo[3,2-a]pyrimidine-5-one.

EXAMPLE 14

2-chloro-7-chloromethyl-5H-thiazolo[3,2-a]pyrimidine-5-one, (6.07 g), prepared according to Example 5, was reacted with sulfuryl chloride (3.8 g) in dichloroethane (150 ml) under stirring at room temperature for 4 hours. The reaction mixture was treated with 5% aqueous NaHCO$_3$ solution then the organic phase was separated and evaporated in vacuo to dryness. Crystallization from methanol gave 5.6 g of 2,6-dichloro-7-chloromethyl-5H-thiazolo[3,2-a]pyrimidine-5-one, m.p. 117°–119° C. dec., which was reacted with triphenylphosphine (5.95 g) in acetonitrile (115 ml) at the reflux temperature for 20 hours. The solution was evaporated in vacuo to dryness and the residue was purified with isopropyl ether to give 10.4 g of [2,6-dichloro-5H-thiazolo[3,2-a]pyrimidine-5-one-7-yl]-methyl-triphenylphosphonium chloride, which was suspended in dimethylsulfoxide (50 ml) and treated with potassium tert-butoxide (2.41 g) dissolved in dimethylsulfoxide (45 ml) at room temperature.

The solution of the ylide so obtained was reacted with 3-pyridine-carboxaldehyde (2.36 g) at room temperature for 20 hours. The reaction mixture was diluted with ice water, neutralized with NaH$_2$PO$_4$ and the precipitate was filtered: crystallization from methanol gave 3.45 g of 2,6-dichloro-7-trans-[2-(3-pyridyl)-ethenyl]-5H-thiazolo[3,2-a]pyrimidine-5-one, m.p. 242°–243° C.; NMR (CDCl$_3$) δ ppm: 7.33 (dd) (1H, C-5 pyridyl proton), 7.51 (d) (1H, β-ethenyl proton), 7.83 (s) (1H, C-3 proton), 7.88 (d) (1H, α-ethenyl proton), 7.91 (dt) (1H, C-4 pyridyl proton), 8.58 (bd) (1H, C-6 pyridyl proton), 8.80 (bs) (1H, C-2 pyridyl proton); $J_{H\alpha H\beta} = 16$ Uz.

By proceeding analogously the following compounds were prepared:

6-chloro-3-methyl-7-trans-[2-(3-pyridyl)-ethenyl]-5H-thiazolo[3,2-a]pyrimidine-5-one, m.p. 219°–220° C.;
6-chloro-2,3-dimethyl-7-trans-[2-(3-pyridyl)-ethenyl]-5H-thiazolo[3,2-a]pyrimidine-5-one, m.p. 226°–228° C.;
6-chloro-3-phenyl-7-trans-[2-(3-pyridyl)-ethenyl]-5H-thiazolo[3,2-a]pyrimidine-5-one, m.p. 203°–204° C.;
6-chloro-3-(4-chloro-phenyl)-7-trans-[2-(3-pyridyl)-ethenyl]-5H-thiazolo[3,2-a]pyrimidine-5-one, m.p. 278°–280° C.;
6-chloro-3-(4-methoxy-phenyl)-7-trans-[2-(3-pyridyl)-ethenyl]-5H-thiazolo[3,2-a]pyrimidine-5-one, m.p. 264°–265° C.;
6-chloro-3-(4-fluoro-phenyl)-7-trans-[2-(3-pyridyl)-ethenyl]-5H-thiazolo[3,2-a]pyrimidine-5-one, m.p. 268°–269° C.;
6-chloro-3-(4-methyl-phenyl)-7-trans-[2-(3-pyridyl)-ethenyl]-5H-thiazolo[3,2-a]pyrimidine-5-one, m.p. 258°–259° C.;
6-chloro-3-(3-methoxy-phenyl)-7-trans-[2-(3-pyridyl)-ethenyl]-5H-thiazolo[3,2-a]pyrimidine-5-one;
6-chloro-3-(2-methoxy-phenyl)-7-trans-[2-(3-pyridyl)-ethenyl]-5H-thiazolo[3,2-a]pyrimidine-5-one;
6-chloro-3-(2-thienyl)-7-trans-[2-(3-pyridyl)-ethenyl]-5H-thiazolo[3,2-a]pyrimidine-5-one;
6-chloro-3-tert.butyl-7-trans-[2-(3-pyridyl)-ethenyl]-5H-thiazolo[3,2-a]pyrimidine-5-one;
6-chloro-3-trifluoromethyl-7-trans-[2-(3-pyridyl)-ethenyl]-5H-thiazolo[3,2-a]pyrimidine-5-one, m.p. 247°–249° C.;
6-chloro-3-(3,4-ethylenedioxy-phenyl)-7-trans-[2-(3-pyridyl)-ethenyl]-5H-thiazolo[3,2-a]pyrimidine-5-one;
6-chloro-3-(3,4-dimethoxy-phenyl)7-trans-[2-(3-pyridyl)-ethenyl]-5H-thiazolo[3,2-a]pyrimidine-5-one;
6-chloro-3-(2,4-dimethoxy-phenyl)-7-trans-[2-(3-pyridyl)-ethenyl]-5H-thiazolo[3,2-a]pyrimidine-5-one;
6-chloro-2-methyl-3-phenyl-7-trans-[2-(3-pyridyl)-ethenyl]-5H-thiazolo[3,2-a]pyrimidine-5-one, m.p. 229°–232° C.;
6-chloro-2-cyano-7-trans-[2-(3-pyridyl)-ethenyl]-5H-thiazolo[3,2-a]pyrimidine-5-one;
6-chloro-3-(3-pyridyl)-7-trans-[2-(3-pyridyl)-ethenyl]-5H-thiazolo[3,2-a]pyrimidine-5-one, m.p. 274°–275° C.;
6-chloro-3-(2-pyridyl)-7-trans-[2-(3-pyridyl)-ethenyl]-5H-thiazolo[3,2-a]pyrimidine-5-one;
6-chloro-3-(4-pyridyl)-7-trans-[2-(3-pyridyl)-ethenyl]-5H-thiazolo[3,2-a]pyrimidine-5-one;
6-chloro-3-(4-biphenylyl)-7-trans-[2-(3-pyridyl)-ethenyl]-5H-thiazolo[3,2-a]pyrimidine-5-one;
6-chloro-3-(2-naphthyl)-7-trans-[2-(3-pyridyl)-ethenyl]-5H-thiazolo[3,2-a]pyrimidine-5-one;
6-chloro-3-(2-nitro-phenyl)-7-trans-[2-(3-pyridyl)-ethenyl]-5H-thiazolo[3,2-a]pyrimidine-5-one;
6-chloro-3-(2-amino-phenyl)-7-trans-[2-(3-pyridyl)-ethenyl]-5H-thiazolo[3,2-a]pyrimidine-5-one;
6-chloro-3-(3-amino-phenyl)-7-trans-[2-(3-pyridyl)-ethenyl]-5H-thiazolo[3,2-a]pyrimidine-5-one;
6-chloro-3-(4-amino-phenyl)-7-trans-[2-(3-pyridyl)-ethenyl]-5H-thiazolo[3,2-a]pyrimidine-5-one;
6-chloro-7-trans-[2-(2-methyl-5-thiazolyl)-ethenyl]-5H-thiazolo[3,2-a]pyrimidine-5-one, m.p. 230°–233° C.;
2,6-dichloro-7-trans-[2-(2-methyl-5-thiazolyl)-ethenyl]-5H-thiazolo[3,2-a]pyrimidine-5-one;

6-chloro-3-methyl-7-trans-[2-(2-methyl-5-thiazolyl)-ethenyl]-5H-thiazolo[3,2-a]pyrimidine-5-one;

6-chloro-2,3-dimethyl-7-trans-[2-(2-methyl-5-thiazolyl)-ethenyl]-5H-thiazolo[3,2-a]pyrimidine-5-one;

6-chloro-7-trans-[2-(2-methyl-5-thiazolyl)-ethenyl]-3-phenyl-5H-thiazolo[3,2-a]pyrimidine-5-one, m.p. 190°-192° C.;

6-chloro-7-trans-[2-(2-methyl-5-thiazolyl)-ethenyl]-3-trifluoromethyl-5H-thiazolo[3,2-a]pyrimidine-5-one; and 6-chloro-7-trans-[2-(2-methyl-5-thiazolyl)-ethenyl]-3-(3-pyridyl)-5H-thiazolo[3,2-a]pyrimidine-5-one.

EXAMPLE 15

4-carbethoxymethyl-2-amino-thiazole (14 g) was reacted with ethyl 4-chloro-acetoacetate (19.3 g) in polyphosphoric acid (70 g) under stirring at 100° C. for 2.5 hours. After cooling, dilution with ice water and neutralization, the precipitate was filtered and washed with water: the obtained 3-carbethoxymethyl-7-chloromethyl-5H-thiazolo[3,2-a]pyrimidine-5-one, m.p. 94°-95° C. (19 g) was reacted with triphenyl-phosphine (19.1 g) in acetonitrile (100 ml) under stirring at reflux temperature for 20 hours. After cooling the precipitate was filtered and washed with isopropyl ether to give (3-carbethoxymethyl-5H-thiazolo[3,2-a]pyrimidine-5-one-7-yl)-methyl-triphenylphosphonium chloride, m.p. 295° C. dec. (15 g), which was added under stirring to a suspension of 75% NaH (1.31 g) in dichloroethane (100 ml) and dimethylsulphoxide (100 ml) and reacted with 3-pyridine-carboxaldehyde (5.76 g) at 25° C. for 6 hours.

The reaction mixture was diluted with ice water, neutralized to pH 6 with NaH$_2$PO$_4$ and extracted with dichloroethane: after evaporation in vacuo to dryness the residue was crystallized from methanol to give 7-trans-[2-(3-pyridyl)-ethenyl]-5-oxo-5H-thiazolo[3,2-a]pyrimidine-3-acetic acid, ethyl ester, m.p. 185°-187° C. (5.35 g), which was heated with 37% HCl (60 ml) and acetic acid (60 ml) at reflux temperature for 1 hour; after cooling, dilution with ice water and neutralization to pH 6 with 35% NaOH, the precipitate was filtered and crystallized from dimethylformamide-water to give 3.3 g of 7-trans-[2-(3-pyridyl)-ethenyl]-5-oxo-5H-thiazolo[3,2-a]pyrimidine-3-acetic acid, m.p. 300° C. dec.

NMR (CF$_3$COOD) δppm: 4.61 (bs) (2H, CH$_2$COOH), 7.07 (s) (1H, C-6 proton), 7.66 (d) (1H, β-ethenyl proton), 7.68 (s) (1H, C-2 proton), 8.06 (d) (1H, α-ethenyl proton), 8.40 (dd) (1H, C-5 pyridyl proton), 9.09 (m) (2H, C-4 and C-6 pyridyl protons), 9.37 (bs) (1H, C-2 pyridyl proton); J$_{HαHβ}$=16 Hz.

By proceeding analogously, using the suitable aldehydes, the following compounds were prepared:

7-trans-[2-(2-pyridyl)-ethenyl]-5-oxo-5H-thiazolo[3,2-a]pyrimidine-3-acetic acid;

7-trans-[2-(4-pyridyl)-ethenyl]-5-oxo-5H-thiazolo[3,2-a]pyrimidine-3-acetic acid;

7-trans-[2-(6-methyl-2-pyridyl)-ethenyl]-5-oxo-5H-thiazolo[3,2-a]pyrimidine-3-acetic acid;

7-trans-[2-(2-methyl-5-thiazolyl)-ethenyl]-5-oxo-5H-thiazolo[3,2-a]pyrimidine-3-acetic acid;

7-trans-[2-(1-methyl-2-pyrrolyl)-ethenyl]-5-oxo-5H-thiazolo[3,2-a]pyrimidine-3-acetic acid;

7-trans-(2-phenyl-ethenyl)-5-oxo-5H-thiazolo[3,2-a]pyrimidine-3-acetic acid, m.p. 252°-255° C.;

7-trans-[2-(4-methoxy-phenyl)-ethenyl]-5-oxo-5H-thiazolo[3,2-a]pyrimidine-3-acetic acid;

7-trans-[2-(4-chloro-phenyl)-ethenyl]-5-oxo-5H-thiazolo[3,2-a]pyrimidine-3-acetic acid;

7-trans-[2-(2,6-dichloro-phenyl)-ethenyl]-5-oxo-5H-thiazolo[3,2-a]pyrimidine-3-acetic acid; and 7-trans-[2-(2,4-dichloro-phenyl)-ethenyl]-5-oxo-5H-thiazolo[3,2-a]pyrimidine-3-acetic acid.

EXAMPLE 16

By proceeding according to Example 9, starting from suitable 6-substituted-5H-thiazolo[3,2-a]pyrimidine-5-ones, the following compounds were prepared:

6-methyl-7-trans-[2-(3-pyridyl)-ethenyl]-5-oxo-5H-thiazolo[3,2-a]pyrimidine-3-acetic acid;

6-chloro-7-trans-[2-(2-pyridyl)-ethenyl]-5-oxo-5H-thiazolo[3,2-a]pyrimidine-3-acetic acid;

6-chloro-7-trans-[2-(4-pyridyl)-ethenyl]-5-oxo-5H-thiazolo[3,2-a]pyrimidine-3-acetic acid;

6-chloro-7-trans-[2-(6-methyl-2-pyridyl)-ethenyl]-5-oxo-5H-thiazolo[3,2-a]pyrimidine-3-acetic acid;

6-chloro-7-trans-[2-(2-methyl-5-thiazolyl)-ethenyl]-5-oxo-5H-thiazolo[3,2-a]pyrimidine-3-acetic acid;

6-chloro-7-trans-[2-(1-methyl-2-pyrrolyl)-ethenyl]-5-oxo-5H-thiazolo[3,2-a]pyrimidine-3-acetic acid;

6-methyl-7-trans-[2-(4-methoxy-phenyl)-ethenyl]-5-oxo-5H-thiazolo[3,2-a]pyrimidine-3-acetic acid;

6-methyl-7-trans-[2-(4-chloro-phenyl)-ethenyl]-5-oxo-5H-thiazolo[3,2-a]pyrimidine-3-acetic acid;

6-methyl-7-trans-(2-phenyl-ethenyl)-5-oxo-5H-thiazolo[3,2-a]pyrimidine-3-acetic acid;

6-chloro-7-trans-[2-(2,6-dichloro-phenyl)-ethenyl]-5-oxo-5H-thiazolo[3,2-a]pyrimidine-3-acetic acid;

6-chloro-7-trans-[2-(3-pyridyl)-ethenyl]-5-oxo-5H-thiazolo[3,2-a]pyrimidine-3-acetic acid, m.p. 320°-330° C. dec., NMR (CDCl$_3$—CF$_3$COOD) δp.p.m.: 4.30 (s) (2H, —CH$_2$COO—), 7.11 (s) (1H, C-2 proton), 7.73 (d) (1H, β-ethenyl proton), 7.98 (d) (1H, α-ethenyl proton), 8.09 (m) (1H, C-5 pyridyl proton), 8.80 (m) (2H, C-4 and C-6 pyridyl protons), 9.08 (bs) (1H, C-2 pyridyl proton); J$_{HαHβ}$=16 Hz; 6-chloro-7-trans-(2-phenyl-ethenyl)-5-oxo-5H-thiazolo[3,2-a]pyrimidine-3-acetic acid, m.p. 301°-303° C., and 6-chloro-7-trans-[2-(4-methoxy-phenyl)-ethenyl]-5-oxo-5H-thiazolo[3,2-a]pyrimidine-3-acetic acid.

EXAMPLE 17

7-methyl-5H-thiazolo[3,2-a]pyrimidine-5-one, m.p. 127°-129° C., (4 g), prepared according to Example 1 using ethyl acetoacetate, dissolved in benzene (100 ml) was reacted with N-bromo-succinimide (4.7 g) under stirring at room temperature for 1 hour. The precipitate was dissolved by adding chloroform and the solution was washed with water: evaporation in vacuo to dryness and crystallization of the residue from methanol gave 6-bromo-7-methyl-5H-thiazolo[3,2-a]pyrimidine-5-one, m.p. 233°-234° C. (5.1 g), which was reacted with 3-pyridine-carboxaldehyde (3.4 g) in methanol (190 ml) in the presence of sodium methoxide (2.2 g) under stirring at the reflux temperature for 2 hours. After cooling the precipitate was filtered and washed with water until neutral: crystallization from CH$_2$Cl$_2$-methanol gave 5.18 g of 6-bromo-7-trans-[2-(3-pyridyl)-ethenyl]-5H-thiazolo[3,2-a]pyrimidine-5-one, m.p. 208°-209° C., NMR (CDCl$_3$) δppm: 6.99 (d) (1H, C-2 proton), 7.33 (dd) (1H, C-5 pyridyl proton), 7.59 (d) (1H, β-ethenyl proton), 7.95 (d) (1H, α-ethenyl proton), 7.96 (d) (1H, C-3 proton), 7.98 (m) (1H, C-4 pyridyl proton), 8.58 (bd) (1H, C-6 pyridyl proton), 8.82 (bs) (1H, C-2 pyridyl proton); $J_{H\alpha H\beta}=16$ Hz.

By proceeding analogously the following compounds were prepared:

6-bromo-7-trans-[2-(2-pyridyl)-ethenyl]-5H-thiazolo[3,2-a]pyrimidine-5-one;

6-bromo-7-trans-[2-(4-pyridyl)-ethenyl]-5H-thiazolo[3,2-a]pyrimidine-5-one; and 6-bromo-trans-[2-(6-methyl-2-pyridyl)-ethenyl]-5H-thiazolo[3,2-a]pyrimidine-5-one.

EXAMPLE 18

7-trans-[2-(2-nitro-phenyl)-ethenyl]-5H-thiazolo[3,2-a]pyrimidine-5-one (10 g), obtained according to Example 4, was reacted with $SnCl_2.2H_2O$ (74 g) in 37% HCl (45 ml) and acetic acid (135 ml) under stirring at 60° C. for 24 hours. After cooling the precipitate was filtered, washed with water until neutral and then suspended under stirring in 2.5% aqueous $NaHCO_3$ solution (300 ml). The precipitate was filtered and washed with water until neutral: after purification with hot chloroform 5.5 g of 7-trans-[2-(2-amino-phenyl)-ethenyl]-5H-thiazolo[3,2-a]pyrimidine-5-one, m.p. 246°–248° C., were obtained; NMR ($CDCl_3$-DMSO d6-$CF_3$ COOD) δppm: 6.62 (s) (1H, C-6 proton), 7.10 (d) (1H, β-ethenyl proton), 7.48 (d) (1H, C-2 proton), 7.55 (m) (3H, C-3, C-4 and C-5 phenyl protons), 7.88 (m) (1H, C-6 phenyl proton), 8.16 (d) (1H, α-ethenyl proton), 8.18 (d) (1H, C-3 proton); $J_{H\alpha H\beta}=16$ Hz.

By proceeding analogously the following compounds were prepared:

3-(4-amino-phenyl)-7-trans-[2-(3-pyridyl)-ethenyl]-5H-thiazolo[3,2-a]pyrimidine-5-one, m.p. 282°–284° C. (dec);

3-(3-amino-phenyl)-7-trans-[2-(3-pyridyl)-ethenyl]-5H-thiazolo[3,2-a]pyrimidine-5-one.

EXAMPLE 19

7-trans-[2-(4-hydroxy-3-iodo-phenyl)-ethenyl]-5H-thiazolo[3,2-a]pyrimidine-5-one (1.4 g), prepared according to Example 4, was reacted with acetic anhydride (2.8 ml) in pyridine (5.6 ml) and dimethylacetamide (30 ml) under stirring at room temperature for 2 hours. After dilution with ice water the precipitate was filtered and washed with water until neutral: crystallization from dioxane gave 1.2 g of 7-trans-[2-(4-acetoxy-3-iodo-phenyl)-ethenyl]-5H-thiazolo[3,2-a]pyrimidine-5-one, m.p. 272°–275° C., NMR ($CDCl_3$—$CF_3COOD$) δppm: 2.52 (s) (3H, —$OCOCH_3$), 6.91 (s) (1H, C-6 proton), 7.03 (d) (1H, β-ethenyl proton), 7.22 (d) (1H, C-5 phenyl proton), 7.66 (d) (1H, α-ethenyl proton), 7.67 (d) (1H, C-2 proton), 7.67 (dd) (1H, C-6 phenyl proton), 8.13 (d) (1H, C-2 phenyl proton), 8.37 (d) (1H, C-3 proton); $H_{H\alpha H\beta}=16$ Hz.

By proceeding analogously, the following compounds were prepared:

7-trans-[2-(2-N-acetylamino-phenyl)-ethenyl]-5H-thiazolo[3,2-a]pyrimidine-5-one, m.p. 240°–242° C.;

3-(4-N-acetylamino-phenyl)-7-trans-[2-(3-pyridyl)-ethenyl]-5H-thiazolo[3,2-a]pyrimidine-5-one, m.p. 278°–280° C. (dec);

3-(3-N-acetylamino-phenyl)-7-trans-[2-(3-pyridyl)-ethenyl]-5H-thiazolo[3,2-a]pyrimidine-5-one; and 3-(2-N-acetylamino-phenyl)-7-trans-[2-(3-pyridyl)-ethenyl]-5H-thiazolo[3,2-a]pyrimidine-5-one.

EXAMPLE 20

Trimethyl-sulphoxonium iodide (10.4 g) was reacted with 50% sodium hydride (2.25 g) in dimethylformamide (50 ml) under stirring at room temperature for 1 hour, then a solution of 7-trans-[2-(3-pyridyl)-ethenyl]-5H-thiazolo[3,2-a]pyrimidine-5-one (6 g) in dimethylformamide (50 ml) was added.

The mixture was allowed to react under stirring at room temperature for 20 hours, then it was diluted with ice water, neutralized with $NaH_2PO_4$ and extracted with chloroform. After evaporation in vacuo the crude residue was purified over a $SiO_2$ column using ethyl acetate as eluent: crystallization from ethyl acetate gave 2.35 g of 7-trans-[2-(3-pyridyl)-cyclopropyl]-5H-thiazolo[3,2-a]pyrimidine-5-one, m.p. 115°–117° C., NMR ($CDCl_3$) δppm: 1.50 (m) (1H,

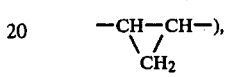

1.89 (m) and 2.16 (m)

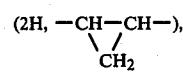

2.68

(m) (1H, 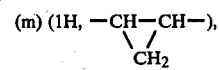

6.28 (s) (1H, C-6 proton), 7.02 (d) (1H, C-2 proton), 7.1–7.5 (m) (2H, C-4 and C-5 pyridyl protons), 8.00 (d) (1H, C-3 proton), 8.5 (m) (2H, C-2 and C-6 pyridyl protons).

By proceeding analogously the following compounds were prepared:

6-methyl-7-trans-[2-(4-pyridyl)-cyclopropyl]-5H-thiazolo[3,2-a]pyrimidine-5-one;

6-methyl-7-trans-[2-(3-pyridyl)-cyclopropyl]-5H-thiazolo[3,2-a]pyrimidine-5-one, m.p. 151°–152° C.;

6-ethyl-7-trans-[2-(3-pyridyl)-cyclopropyl]-5H-thiazolo[3,2-a]pyrimidine-5-one;

2-phenyl-7-trans-[2-(3-pyridyl)-cyclopropyl]-5H-thiazolo[3,2-a]pyrimidine-5-one;

6-methyl-7-trans-[2-(4-methyl-phenyl)-cyclopropyl]-5H-thiazolo[3,2-a]pyrimidine-5-one, m.p. 153°–155° C.;

6-methyl-7-trans-[2-(2-methoxy-3-ethoxy-phenyl)-cyclopropyl]-5H-thiazolo[3,2-a]pyrimidine-5-one;

7-trans-[2-(1-methyl-2-pyrrolyl)-cyclopropyl]-5H-thiazolo[3,2-a]pyrimidine-5-one;

3-methyl-7-trans-[2-(3-pyridyl)-cyclopropyl]-5H-thiazolo[3,2-a]pyrimidine-5-one;

3,6-dimethyl-7-trans-[2-(3-pyridyl)-cyclopropyl]-5H-thiazolo[3,2-a]pyrimidine-5-one;

2-chloro-7-trans-[2-(3-pyridyl)-cyclopropyl]-5H-thiazolo[3,2-a]pyrimidine-5-one;

7-trans-[2-(3-pyridyl)-cyclopropyl]-5-oxo-5H-thiazolo[3,2-a]pyrimidine-3-acetic acid;

7-trans-(2-phenyl-cyclopropyl)-5-oxo-5H-thiazolo[3,2-a]pyrimidine-3-acetic acid;

6-chloro-7-trans-[2-(3-pyridyl)-cyclopropyl]-5-oxo-5H-thiazolo[3,2-a]pyrimidine-3-acetic acid;

6-methyl-7-trans-[2-(3-pyridyl)-cyclopropyl]-5-oxo-5H-thiazolo[3,2-a]pyrimidine-3-acetic acid;

2,3,6-trimethyl-7-trans-[2-(3-pyridyl)-cyclopropyl]-5H-thiazolo[3,2-a]pyrimidine-5-one, m.p. 120° C. dec;

6-chloro-7-trans-[2-(3-pyridyl)-cyclopropyl]-5H-thiazolo[3,2-a]pyrimidine-5-one, m.p. 159°–161° C.;

6-chloro-3-phenyl-7-trans-[2-(3-pyridyl)-cyclopropyl]-5H-thiazolo[3,2-a]pyrimidine-5-one; m.p. 136°–138° C.;

6-chloro-7-trans-[2-(2-methyl-5-thiazolyl)-cyclopropyl]-5H-thiazolo[3,2-a]pyrimidine-5-one, m.p. 174°–175° C.;

6-methyl-2-phenyl-7-trans-[2-(3-pyridyl)-cyclopropyl]-5H-thiazolo[3,2-a]pyrimidine-5-one, m.p. 210°–213° C.;

6-methoxy-7-trans-[2-(3-pyridyl)-cyclopropyl]-5H-thiazolo[3,2-a]pyrimidine-5-one, m.p. 92°–95° C.;

2-chloro-6-methoxy-7-trans-[2-(3-pyridyl)-cyclopropyl]-5H-thiazolo[3,2-a]pyrimidine-5-one;

6-methyl-7-trans-[2-(2-pyridyl)-cyclopropyl]-5H-thiazolo[3,2-a]pyrimidine-5-one;

6-methyl-7-trans-[2-(6-methyl-2-pyridyl)-cyclopropyl]-5H-thiazolo[3,2-a]pyrimidine-5-one;

6-chloro-7-trans-[2-(3-pyridyl)-cyclopropyl]-3-trifluoromethyl-5H-thiazolo[3,2-a]pyrimidine-5-one;

6-chloro-7-trans-[2-(3-pyridyl)-cyclopropyl]-3-(2-thienyl)-5H-thiazolo[3,2-a]pyrimidine-5-one;

6-chloro-3-(3-pyridyl)-7-trans-[2-(3-pyridyl)-cyclopropyl]-5H-thiazolo[3,2-a]pyrimidine-5-one;

6-chloro-3-(2-pyridyl)-7-trans-[2-(3-pyridyl)-cyclopropyl]-5H-thiazolo[3,2-a]pyrimidine-5-one;

6-chloro-3-(4-pyridyl)-7-trans-[2-(3-pyridyl)-cyclopropyl]-5H-thiazolo[3,2-a]pyrimidine-5-one;

6-chloro-3-(4-biphenylyl)-7-trans-[2-(3-pyridyl)-cyclopropyl]-5H-thiazolo[3,2-a]pyrimidine-5-one;

6-chloro-3-phenyl-7-trans-[2-(3-pyridyl)-cyclopropyl]-5H-thiazolo[3,2-a]pyrimidine-5-one;

6-chloro-3-(4-chloro-phenyl)-7-trans-[2-(3-pyridyl)-cyclopropyl]-5H-thiazolo[3,2-a]pyrimidine-5-one;

6-chloro-3-(4-methyl-phenyl)-7-trans-[2-(3-pyridyl)-cyclopropyl]-5H-thiazolo[3,2-a]pyrimidine-5-one; and 6-chloro-3-(4-methoxy-phenyl)-7-trans-[2-(3-pyridyl)cyclopropyl]-5H-thiazolo[3,2-a]pyrimidine-5-one.

EXAMPLE 21

7-trans-(2-phenyl-ethenyl)-5-oxo-5H-thiazolo[3,2-a]pyrimidine-3-acetic acid (1.2 g) was reacted with thionyl chloride (0.6 ml) in dioxane (12 ml) at reflux temperature for 2 hours, then the mixture was evaporated to dryness in vacuo. The residue was reacted with excess of ethanol at 50° C. for 30 minutes, then the solution was concentrated in vacuo and the residue diluted with ice water. The precipitate was filtered and washed with water: crystallization from $CH_2Cl_2$-isopropyl ether gave 0.85 g of 7-trans-(2-phenyl-ethenyl)-5-oxo-5H-thiazolo[3,2-a]pyrimidine-3-acetic acid, ethyl ester, m.p. 252°–255° C., NMR ($CDCl_3$) δppm. 1.29 (t) (3H, —$CH_2CH_3$), 4.12 (bs) (2H,—$CH_2COO$—), 4.22 (q) (2H, —$\underline{CH_2}CH_3$), 6.13 (s) (1H, C-6 proton), 6.62 (bs) (1H, C-2 proton), 6.85 (d) (1H, β-ethenyl proton), 7.2–7.7 (m) (5H, phenyl protons), 7.75 (d) (1H, β-ethenyl proton); $J_{H\alpha H\beta}=16$ Hz.

By proceeding analogously the following compound was prepared:

6-chloro-7-trans-(2-phenyl-ethenyl)-5-oxo-5H-thiazolo[3,2-a]pyrimidine-3-acetic acid, ethyl ester, m.p. 214°–217° C.

EXAMPLE 22

7-trans-[2-(3-pyridyl)-ethenyl]-5-oxo-5H-thiazolo[3,2-a]pyrimidine-3-acetic acid (0.8 g) was reacted with ethyl iodide (0.65 g) and anhydrous $K_2CO_3$ (0.65 g) in dimethylformamide (7 ml) under stirring at room temperature for 6 hours. After dilution with ice water the precipitate was filtered and washed with water until neutral: crystallization from methanol gave 0.55 g pf 7-trans-[2-(3-pyridyl)-ethenyl]-5-oxo-5H-thiazolo[3,2-a]pyrimidine-3-acetic acid, ethyl ester, m.p. 185°–187° C., NMR ($CDCl_3$) δppm. 1.29 (t) (3H, —$CH_2CH_3$), 4.14 (s) (2H, —$CH_2$—COO—), 4.33 (q) (2H, —$\underline{CH_2}CH_3$), 6.16 (s) (1H, C-6 proton), 6.66 (s) (1H, C-2 proton), 6.90 (d) (1H, β-ethenyl proton), 7.30 (dd) (1H, C-5 pyridyl proton), 7.75 (d) (1H, C-4 pyridyl proton), 7.89 (ddd) (1H, C-6 pyridyl proton), 8.54 (ddd) (1H, C-2 pyridyl proton), 8.87 (dd) (1H, β-ethenyl proton); $J_{H\alpha H\beta}=16$ Hz.

By proceeding analogously the following compound was prepared:

6-chloro-7-trans-[2-(3-pyridyl)-ethenyl]-5-oxo-5H-thiazolo[3,2-a]pyrimidine-3-acetic acid, ethyl ester, m.p. 242°–243° C.

EXAMPLE 23

6-hydroxy-7-trans-[2-(3-pyridyl)-ethenyl]-5H-thiazolo[3,2-a]pyrimidine-5-one (2.7 g) dissolved in dimethylformamide (40 ml) was reacted with methyl iodide (2.12 g) in the presence of anhydrous $K_2CO_3$ (2.07 g) under stirring at 50° C. for 5 hours.

After cooling the reaction mixture was diluted with ice water and the precipitate was filtered and washed with water: crystallization from 50% ethanol gave 2.05 g of 6-methoxy-7-trans-[2-(3-pyridyl)-ethenyl]-5H-thiazolo[3,2-a]pyrimidine-5-one, m.p. 186°–187° C.

EXAMPLE 24

By proceeding according to Examples 21 and 22, the isopropyl and n-butyl esters of the following compounds were prepared:

7-trans-(2-phenyl-ethenyl)-5-oxo-5H-thiazolo[3,2-a]pyrimidine-3-acetic acid;

7-trans-[2-(3-pyridyl)-ethenyl]-5-oxo-5H-thiazolo[3,2-a]pyrimidine-3-acetic acid;

6-chloro-7-trans-(2-phenyl-ethenyl)-5-oxo-5H-thiazolo[3,2-a]pyrimidine-3-acetic acid; and 6-chloro-7-trans-[2-(3-pyridyl)-ethenyl]-5-oxo-5H-thiazolo[3,2-a]pyrimidine-3-acetic acid.

EXAMPLE 25

6-methoxy-7-trans-[2-(3-pyridyl)-ethenyl]-5H-thiazolo[3,2-a]pyrimidine-5-one (2.3 g) was dissolved in ethyl acetate and treated with the stoichiometric amount of gaseous HCl in ether: the precipitate was filtered and washed with ethyl acetate to give 2.1 g of 6-methoxy-7-trans-[2-(3-pyridyl)-ethenyl]-5H-thiazolo[3,2-a]pyrimidine-5-one hydrochloride, m.p. 205°–210° C. dec.

By proceeding analogously the following compounds were prepared:

2-chloro-6-methoxy-7-trans-[2-(3-pyridyl)-ethenyl]-5H-thiazolo[3,2-a]pyrimidine-5-one hydrochloride;

2-chloro-7-trans-[2-(3-pyridyl)-ethenyl]-5H-thiazolo[3,2-a]pyrimidine-5-one hydrochloride; and 6-methyl-7-trans-[2-(3-pyridyl)-ethenyl]-5H-thiazolo[3,2-a]pyrimidine-5-one hydrochloride.

EXAMPLE 26

7-trans-(2-phenyl-ethenyl)-5-oxo-5H-thiazolo[3,2-a]pyrimidine-3-acetic acid was treated with the stoichiometric amount of NaHCO$_3$ in a little water at 60° C. for 10 minutes: the solution was concentrated in vacuo to dryness then was diluted with acetone. The precipitate was filtered and washed with acetone: 7-trans-(2-phenyl-ethenyl)-5-oxo-5H-thiazolo[3,2-a]pyrimidine-3-acetic acid, sodium salt, m.p. >300° C., was obtained.

By proceeding analogously the following compounds were prepared:

7-trans-[2-(3-pyridyl)-ethenyl]-5-oxo-5H-thiazolo[3,2-a]pyrimidine-3-acetic acid, sodium salt;

6-chloro-7-trans-[2-(3-pyridyl)-ethenyl]-5-oxo-5H-thiazolo[3,2-a]pyrimidine-3-acetic acid, sodium salt; and 6-chloro-7-trans-(2-phenyl-ethenyl)-5-oxo-5H-thiazolo[3,2-a]pyrimidine-3-acetic acid, sodium salt.

EXAMPLE 27

Tablets, each weighing 200 mg and containing 100 mg of the active substance are manufactured as follows:

| Compositions (for 10.000 tablets) | |
|---|---|
| 2-chloro-7-trans-[2-(3-pyridyl)-ethenyl]-5H-thiazolo[3,2-a]pyrimidine-5-one | 1000 g |
| Lactose | 710 g |
| Corn starch | 237.5 g |
| Talc powder | 37.5 g |
| Magnesium stearate | 15 g |

2-chloro-7-trans-[2-(3-pyridyl)-ethenyl]-5H-thiazolo[3,2-a]pyrimidine-5-one, lactose and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed and processed into tablets using punches of 8 mm diameter.

We claim:

1. A compound having the following general formula (I)

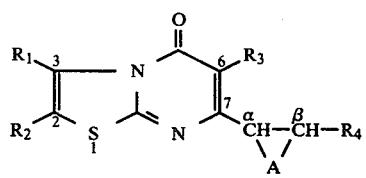

wherein

A completes a bond, thereby providing a double bond between the α- and β-carbon atoms, or A represents a —CH$_2$—group, thereby providing a cyclopropane ring including the α- and β-carbon atoms;

each of R$_1$ and R$_2$ independently represents
- (a) a hydrogen or a halogen atom;
- (b) C$_1$–C$_4$ alkyl, cyano or trifluoromethyl;
- (c) thienyl, pyridyl, biphenyl or naphtyl;
- (d) a phenyl group, unsubstituted or substituted by 1 to 3 substituents chosen from halogen, C$_1$–C$_4$ alkyl, hydroxy, C$_1$–C$_4$ alkoxy, formyloxy, C$_2$–C$_8$ alkanoyloxy, trifluoromethyl, nitro, amino, formylamino, C$_2$–C$_8$ alkanoylamino;
- (e) a phenyl group substituted by one or two C$_1$–C$_4$ alkylenedioxy groups wherein the oxygen atoms are linked to two adjacent carbon atoms of the phenyl ring;
- (f) a group

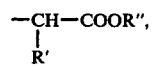

wherein each of R' and R" independently represents a hydrogen atom or a C$_1$–C$_4$ alkyl group;

R$_3$ represents:
- (a') a hydrogen or halogen atom;
- (b') C$_1$–C$_4$ alkyl;
- (c') hydroxy, formyloxy or C$_2$–C$_8$ alkanoyloxy;
- (d') C$_1$–C$_4$ alkoxy or C$_3$–C$_4$ alkenyloxy;

R$_4$ represents:
a pyridyl group, which may be unsubstituted or substituted by C$_1$–C$_4$ alkyl; and the pharmaceutically acceptable salts thereof.

2. A compound of the formula (I) according to claim 1, wherein A is as defined in claim 8; R$_1$ is hydrogen, C$_1$–C$_2$ alkyl, trifluoromethyl, carboxymethyl, pyridyl, biphenyl, naphthyl or phenyl, the phenyl being unsubstituted or substituted as defined in claim 8; R$_2$ is hydrogen, chlorine, bromine, C$_1$–C$_2$ alkyl, cyano, or phenyl, unsubstituted or substituted as defined in claim 8; R$_3$ is hydrogen, chlorine, bromine, C$_1$–C$_3$ alkyl or C$_1$–C$_2$ alkoxy; and R$_4$ represents a pyridyl group unsubstituted or substituted by a methyl group; and the pharmaceutically acceptable salts thereof.

3. A compound selected from the group consisting of:
7-trans-[2-(3-pyridyl)-ethenyl]-5H-thiazolo[3,2-a]pyrimidine-5-one;

2-cyano-7-trans-[2-(3-pyridyl)-ethenyl]-5H-thiazolo[3,2-a]pyrimidine-5-one;

2-chloro-6-methoxy-7-trans-[2-(3-pyridyl)-ethenyl]-5H-thiazolo[3,2-a]pyrimidine-5-one;

2-chloro-6-methyl-7-trans-[2-(3-pyridyl)-ethenyl]-5H-thiazolo[3,2-a]pyrimidine-5-one;

3,6-dimethyl-7-trans-[2-(3-pyridyl)-ethenyl]-5H-thiazolo[3,2-a]pyrimidine-5-one;

2,3,6-trimethyl-7-trans-[2-(3-pyridyl)-ethenyl]-5H-thiazolo[3,2-a]pyrimidine-5-one;

6-methyl-2-phenyl-7-trans-[2-(3-pyridyl)-ethenyl]-5H-thiazolo[3,2-a]pyrimidine-5-one;

6-ethyl-7-trans-[2-(3-pyridyl)-ethenyl]-5H-thiazolo[3,2-a]pyrimidine-5-one;

6-methyl-7-trans-[2-(2-pyridyl)-ethenyl]-5H-thiazolo[3,2-a]pyrimidine-5-one;

6-methyl-7-trans-[2-(6-methyl-2-pyridyl)-ethenyl]-5H-thiazolo[3,2-a]pyrimidine-5-one;

6-methyl-7-trans-[2-(6-methyl-2-pyridyl)-cyclopropyl]-5H-thiazolo[3,2-a]pyrimidine-5-one;

6-methyl-7-trans-[2-(2-pyridyl)-cyclopropyl]-5H-thiazolo[3,2-a]pyrimidine-5-one;
6-methyl-7-trans-[2-(3-pyridyl)-cyclopropyl]-5H-thiazolo[3,2-a]pyrimidine-5-one;
2,6-dichloro-7-trans-[2-(3-pyridyl)-ethenyl]-5H-thiazolo[3,2-a]pyrimidine-5-one;
6-chloro-7-trans-[2-(3-pyridyl)-ethenyl]-5H-thiazolo[3,2-a]pyrimidine-5-one;
6-chloro-3-methyl-7-trans-[2-(3-pyridyl)-ethenyl]-5H-thiazolo[3,2-a]pyrimidine-5-one;
6-chloro-2,3-dimethyl-7-trans-[2-(3-pyridyl)-ethenyl]-5H-thiazolo[3,2-a]pyrimidine-5-one;
6-chloro-3-trifluoromethyl-7-trans-[2-(3-pyridyl)-ethenyl]-5H-thiazolo[3,2-a]pyrimidine-5-one;
6-chloro-3-phenyl-7-trans-[2-(3-pyridyl)-ethenyl]-5H-thiazolo[3,2-a]pyrimidine-5-one;
6-chloro-3-(4-fluoro-phenyl)-7-trans-[2-(3-pyridyl)-ethenyl]-5H-thiazolo[3,2-a]pyrimidine-5-one;
6-chloro-3-(4-chloro-phenyl)-trans-[2-(3-pyridyl)-ethenyl]-5H-thiazolo[3,2-a]pyrimidine-5-one;
6-chloro-3-(4-methyl-phenyl)-7-trans-[2-(3-pyridyl)-ethenyl]-5H-thiazolo[3,2-a]pyrimidine-5-one;
6-chloro-3-(2-methoxy-phenyl)-7-trans-[2-(3-pyridyl)-ethenyl]-5H-thiazolo[3,2-a]pyrimidine-5-one;
6-chloro-3-(3-methoxy-phenyl)-7-trans-[2-(3-pyridyl)-ethenyl]-5H-thiazolo[3,2-a]pyrimidine-5-one;
6-chloro-3-(4-methoxy-phenyl)-7-trans-[2-(3-pyridyl)-ethenyl]-5H-thiazolo[3,2-a]pyrimidine-5-one;
6-chloro-3-(2-thienyl)-7-trans-[2-(3-pyridyl)-ethenyl]-5H-thiazolo[3,2-a]pyrimidine-5-one;
6-chloro-3-(2-pyridyl)-7-trans-[2-(3-pyridyl)-ethenyl]-5H-thiazolo[3,2-a]pyrimidine-5-one;
6-chloro-3-(3-pyridyl)-7-trans-[2-(3-pyridyl)-ethenyl]-5H-thiazolo[3,2-a]pyrimidine-5-one;
6-chloro-3-(4-pyridyl)-7-trans-[2-(3-pyridyl)-ethenyl]-5H-thiazolo[3,2-a]pyrimidine-5-one;
6-chloro-7-trans-[2-(3-pyridyl)-ethenyl]-5-oxo-5H-thiazolo[3,2-a]pyrimidine-3-acetic acid;
3-(4-amino-phenyl)-7-trans-8  2-(3-pyridyl)-ethenyl]-5H-thiazolo[3,2-a]pyrimidine-5-one;
3-phenyl-7-trans-[2-(3-pyridyl)-ethenyl]-5H-thiazolo[3,2-a]pyrimidine-5-one;
3-(4-fluoro-phenyl)-7-trans-[2-(3-pyridyl)-ethenyl]-5H-thiazolo[3,2-a]pyrimidine-5-one;
3-(4-chloro-phenyl)-7-trans-[2-(3-pyridyl)-ethenyl]-5H-thiazolo[3,2-a]pyrimidine-5-one;
3-(3-methoxy-phenyl)-7-trans-[2-(3-pyridyl)-ethenyl]-5H-thiazolo[3,2-a]pyrimidine-5-one;
3-(4-methoxy-phenyl)-7-trans-[2-(3-pyridyl)-ethenyl]-5H-thiazolo[3,2-a]pyrimidine-5-one;
3-(3,4-dimethoxy-phenyl)-7-trans-[2-(3-pyridyl)-ethenyl]-5H-thiazolo[3,2-a]pyrimidine-5-one;
3-(3,4-ethylendioxy-phenyl)-7-trans-[2-(3-pyridyl)-ethenyl]-5H-thiazolo[3,2-a]pyrimidine-5-one;
3-(4-biphenylyl)-7-trans-[2-(3-pyridyl)-ethenyl]-5H-thiazolo[3,2-a]pyrimidine-5-one;
3-(2-naphtyl)-7-trans-[2-(3-pyridyl)-ethenyl]-5H-thiazolo[3,2-a]pyrimdine-5-one;
3-(2-pyridyl)-7-trans-[2-(3-pyridyl)-ethenyl]-5H-thiazolo[3,2-a]pyrimidine-5-one;
3-(3-pyridyl)-7-trans-[2-(3-pyridyl)-ethenyl]-5H-thiazolo[3,2-a]pyrimidine-5-one;
3-(4-pyridyl)-7-trans-[2-(3-pyridyl)-ethenyl]-5H-thiazolo[3,2-a]pyrimidine-5-one;
3-(4-N-acetyl-amino-phenyl)-7-trans-[2-(3-pyridyl)-ethenyl]-5H-thiazolo[3,2-a]pyrimidine-5-one;
7-trans-[2-(3-pyridyl)-ethenyl]-3-(2-thienyl)-5H-thiazolo[3,2-a]pyrimidine-5-one,
and the pharmaceutically acceptable salts thereof.

4. 6-methoxy-7-trans-[2-(3-pyridyl)-ethenyl]-5H-thiazolo[3,2-a]pyrimidine-5-one; and the pharmaceutically accceptable salts thereof.

5. 2-chloro-7-trans-[2-(3-pyridyl)-ethenyl]-5H-thiazolo[3,2-a]pyrimidine-5-one; and the pharmaceutically acceptable salts thereof.

6. 6-methyl-7-trans-[2-(3-pyridyl)-ethenyl]-5H-thiazolo[3,2-a]pyrimidine-5-one; and the pharmaceutically acceptable salts thereof.

7. 3-(4-methyl-phenyl)-7-trans-[2-(3-pyridyl)ethenyl]-5H-thiazolo[3,2-a]pyrimidine-5-one; and the pharmaceutically acceptable salts thereof.

8. 2-methyl-3-phenyl-7-trans-[2-(3-pyridyl)ethenyl]-5H-thiazolo[3,2-a]pyrimidine-5-one; and the pharmaceutically acceptable salts thereof.

9. A method for the treatment of peptic ulcers in a patient comprising administering to the patient an effective amount of a compound according to claim 1.

10. A method for the treatment of excessive gastric secretion in a patient comprising administering to the patient an effective amount of a compound according to claim 1.

11. A method for the treatment of inflammation in a patient comprising administering to the patient an effective amount of a compound according to claim 1.

12. A method for the treatment of pain in a patient comprising administering to the patient an effective amount of a compound according to claim 1.

13. A method for the treatment of thrombosis, peripheral vasculopaties and coronary artery diseases in a patient comprising administering to the patient an effective amount of a compound according to claim 1.

14. A pharmaceutical composition containing a suitable carrier and/or diluent and, as an active principle, a compound of formula (I) according to claim 8, or a pharmaceutically acceptable salt thereof.

* * * * *

UNITED STATES PATENT AND TRADEMARK OFFICE
CERTIFICATE OF CORRECTION

PATENT NO. : 4,444,773
DATED : April 24, 1984
INVENTOR(S) : Gianfederico DORIA et al It is certified that error appears in the above—identified patent and that said Letters Patent is hereby corrected as shown below:

In the Abstract, delete the first appearing structural formula and insert therefor

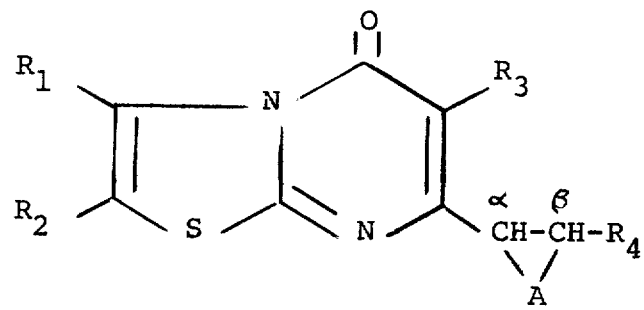

In the Abstract, line 3 after the second appearing structural formula, after "alkenyloxy", insert --or alkoxy--.

Signed and Sealed this

Twenty-sixth Day of March 1985

[SEAL]

Attest:

DONALD J. QUIGG

Attesting Officer          Acting Commissioner of Patents and Trademarks

UNITED STATES PATENT AND TRADEMARK OFFICE
CERTIFICATE OF CORRECTION

PATENT NO. : 4,444,773

DATED : April 24, 1984

INVENTOR(S) : Gianfederico Doria, et al.

It is certified that error appears in the above-identified patent and that said Letters Patent is hereby corrected as shown below:

Column 34, Claim 2, lines 2, 5 and 7 of the claim, delete "claim 8" and insert therefor -- claim 1 -- , in each instance.

Column 35, line 20, delete this line in its entirety and insert therefor -- 6-chloro-3-(4-chloro-phenyl)-7-trans-[2-(3-pyridyl)- -- .

Column 35, line 44, delete this line in its entirety and insert therefor -- 3-(4-amino-phenyl)-7-trans-[2-(3-pyridyl)-ethenyl]- -- .

Column 36, line 8, delete "pyrimdine" and insert therefor -- pyrimidine -- .

Column 36, Claim 4, last line of the claim, delete acceptable" and insert therefor -- acceptable -- .

Column 36, Claim 14, penultimate line, delete "claim 8" and insert therefor -- claim 1 -- .

Signed and Sealed this

Eighth Day of April 1986

[SEAL]

Attest:

DONALD J. QUIGG

Attesting Officer

Commissioner of Patents and Trademarks